United States Patent
Li et al.

(10) Patent No.: US 12,337,129 B2
(45) Date of Patent: Jun. 24, 2025

(54) LONG-ACTING ANTIBACTERIAL ANTI-STENOSIS FUNCTIONAL URETHRAL STENT AND PREPARATION METHOD THEREOF

(71) Applicants: NANTONG TEXTILE & SILK INDUSTRIAL TECHNOLOGY RESEARCH INSTITUTE, Nantong (CN); SOOCHOW UNIVERSITY, Suzhou (CN)

(72) Inventors: Gang Li, Suzhou (CN); Lu Li, Suzhou (CN); Feng Li, Suzhou (CN); Lirong Duan, Suzhou (CN)

(73) Assignees: NANTONG TEXTILE & SILK INDUSTRIAL TECHNOLOGY RESEARCH INSTITUTE, Nantong (CN); SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 18/577,719

(22) PCT Filed: Mar. 22, 2022

(86) PCT No.: PCT/CN2022/082332
§ 371 (c)(1),
(2) Date: Jan. 9, 2024

(87) PCT Pub. No.: WO2023/284329
PCT Pub. Date: Jan. 19, 2023

(65) Prior Publication Data
US 2024/0261548 A1    Aug. 8, 2024

(30) Foreign Application Priority Data
Jul. 15, 2021   (CN) .......................... 202110800298.4

(51) Int. Cl.
*A61L 31/16*   (2006.01)
*A61L 31/02*   (2006.01)
(Continued)

(52) U.S. Cl.
CPC ......... *A61M 27/008* (2013.01); *A61L 31/022* (2013.01); *A61L 31/10* (2013.01);
(Continued)

(58) Field of Classification Search
CPC . D03D 3/02; A61L 31/04; A61L 31/10; A61L 31/00; A61L 31/022; A61L 31/16;
(Continued)

(56) References Cited

U.S. PATENT DOCUMENTS

| | | | |
|---|---|---|---|
| 2010/0256728 A1* | 10/2010 | Rea Peterson | ............ A61F 2/07 623/1.13 |
| 2016/0287374 A1 | 10/2016 | Soletti et al. | |
| 2019/0091442 A1 | 3/2019 | Erbey, II et al. | |

FOREIGN PATENT DOCUMENTS

| | | |
|---|---|---|
| CN | 102488926 A | 6/2012 |
| CN | 102813965 A | 12/2012 |

(Continued)

OTHER PUBLICATIONS

Translation of CN103705325 both an abstract and description (disclosure) (Year: 2014).*
(Continued)

*Primary Examiner* — Brian E Pellegrino
(74) *Attorney, Agent, or Firm* — Bayramoglu Law Offices LLC

(57) ABSTRACT

A long-acting antibacterial anti-stenosis functional urethral stent and preparation method thereof is provided; the urethral stent is a tubular structure consisting of three layers: inner, middle and outer layers; the middle layer is a fabric tube; the outer layer is a silk fibroin film carrying anti-
(Continued)

stenosis drugs; the inner layer is an antibacterial antifouling coating, consisting of chitosan-nanosilica arrays, villi, microvilli and antibacterial drugs; the preparation method includes: after making yarns into the fabric tube by textile molding, preparing the antibacterial and anti-fouling coating on the inner surface, and the silk fibroin film carrying anti-stenosis drugs on the outer surface respectively, to obtain the long-acting antibacterial anti-stenosis functional urethral stent. The method is simple, and the prepared urethral stent has a smooth surface and good biocompatibility, which has excellent properties such as radial compression force, circumferential expansion force, resistance to bending and torsion and elastic recovery.

3 Claims, 5 Drawing Sheets

(51) Int. Cl.
*A61L 31/10* (2006.01)
*A61L 31/14* (2006.01)
*A61M 27/00* (2006.01)
*D03D 3/02* (2006.01)

(52) U.S. Cl.
CPC .............. *A61L 31/14* (2013.01); *A61L 31/16* (2013.01); *D03D 3/02* (2013.01); *A61L 2300/404* (2013.01); *A61L 2300/416* (2013.01); *A61L 2400/18* (2013.01); *A61M 2207/00* (2013.01); *A61M 2210/1089* (2013.01)

(58) Field of Classification Search
CPC ...... A61L 31/14; A61L 2300/404; A61F 2/90; A61F 2210/0076
See application file for complete search history.

(56) References Cited

FOREIGN PATENT DOCUMENTS

| | | | | |
|---|---|---|---|---|
| CN | 103705325 A | * | 4/2014 | |
| CN | 106823012 A | * | 6/2017 | ........... A61L 29/085 |
| CN | 111603614 A | | 9/2020 | |
| CN | 113577401 A | | 11/2021 | |
| WO | WO-2009049494 A1 | * | 4/2009 | .............. A61L 31/10 |

OTHER PUBLICATIONS

Translation of WO 2009049494 (Year: 2009).*
Aranaz et al., Chitosan: An overview of its properties and applications, Sep. 2021, Polymers (Year: 2021).*
Translation of CN 106823012 (Year: 2017).*
YY/T0872—2013, Test methods for ureteral stents, China National Standards, 2013, pp. 1-10, National Medical Products Administration.
ISO 20645:2004, Textile fabrics—Determination of antibacterial activity—Agar diffusion plate test, International Standard, 2004, pp. ii-vi, 1-3.

* cited by examiner

LONG-ACTING ANTIBACTERIAL ANTI-STENOSIS FUNCTIONAL URETHRAL STENT AND PREPARATION METHOD THEREOF

CROSS REFERENCE TO THE RELATED APPLICATIONS

This application is the national phase entry of International Application No. PCT/CN2022/082332, filed on Mar. 22, 2022, which is based upon and claims priority to Chinese Patent Application No. 202110800298.4, filed on Jul. 15, 2021, the entire contents of which are incorporated herein by reference.

TECHNICAL FIELD

The present invention belongs to the technical field of biomedical materials, and more particularly, relates to a long-acting antibacterial anti-stenosis functional urethral stent and preparation method thereof.

BACKGROUND

Urethral stenosis is an intractable disease in urinary surgery and primarily caused by urethral scarring. At present, urethral stenosis is mainly treated by surgical means including urethroplasty, internal urethrotomy, periodic urethral dilatation and etc. However, all these methods have certain limitations: urethroplasty is highly traumatic; internal urethrotomy is greatly traumatic and has a high probability of re-stenosis; periodic urethral dilatation cannot solve the problem fundamentally and causes great suffering to patients. Implanting stents in the urethra can effectively treat urethral stenosis, with advantages such as good mechanical supporting performance, maintaining long-term urethral patency and making patient's urination normal.

Currently common urethral stents include silicone, metal, polyglycolide or polylactic-glycolic acid, collagen and other urethral stents. These types of urethral stents disclosed in the prior art generally suffer from poor antibacterial and anti-stenosis effects.

Therefore, it is of great significance to study a urethral stent with long-acting antibacterial and anti-stenosis functions.

SUMMARY

In order to solve the problems in the background, the invention provides a long-acting antibacterial anti-stenosis functional urethral stent, the entire urethral stent is a three-layer structure composed of inner, middle and outer layers, and plays different roles of each layer to complement each other's advantages; wherein the middle layer is a fabric tube made by textile molding, as a skeleton structure of the urethral stent, and plays a major role in mechanical supporting and maintains the normal urination function of the urethra; wherein the inner layer is to carry an antibacterial chitosan solution inside the fabric tube and perform anti-fouling functional treatment of the inner layer, in order to achieve long-acting antibacterial and anti-proteinosis effect, keep the urethra unobstructed and promote recovery from urethral injury; wherein the outer layer is a silk fibroin membrane that carries anti-stenosis drugs outside the fabric tube, and through regulating the secondary structure of the silk fibroin, the drugs carried on inner and outer layers of the urethral stent can be released in the urethra slowly and stably, thus playing a role of treating stenosis.

To this end, the technical schemes of the invention are as follows:

A long-acting antibacterial anti-stenosis functional urethral stent, wherein the urethral stent is a tubular structure consisting of three layers: inner, middle and outer layers;

wherein the middle layer is a fabric tube, that is a fabric with tubular structure; wherein the outer layer is a silk fibroin film carrying anti-stenosis drugs, and achieves controllable and long-acting release of the carried drug by regulating the β-sheet content in the secondary structure of the silk fibroin; wherein the inner layer is an antibacterial antifouling coating, consisting of chitosan-nanosilica arrays, villi, microvilli and antibacterial drugs;

wherein the chitosan-nanosilica array arranged on the inner surface of the fabric tube, is a nanosilica array carrying chitosan molecules; one end of the villus is fixed on the surface of the chitosan-nanosilica array while the other end is a free end, and a material of the villus is a polymer containing polyhydroxy functional group, which is bonded with the chitosan in the chitosan-nanosilica array through covalent bonds, and a number of hydroxyl of the polymer containing polyhydroxy functional group is greater than or equal to 2; one end of the microvillus is fixed to the villus while the other end is a free end, and a material of the microvillus is a polymer with antibacterial adhesion function, which is bonded with the villus through covalent bonds; wherein the antibacterial drug is distributed in the whole inner layer.

The invention provides a long-acting antibacterial anti-stenosis functional urethral stent, and as the skeleton structure of the entire urethral stent, the middle fabric tube has good mechanical properties such as compression resistance, elastic recovery and bending resistance, ensuring mechanical support and drainage effect; the villi-like structure on the antibacterial antifouling coating on the surface of the stent not only avoids calcification of the inner lumen, deposition of carbonate and other wastes, and adhesion and growth of bacteria, but also increases the specific surface area of the lumen of the urethral stent and carries antibacterial drugs; the villi-like structure on one hand increases the contact space between the inner layer and excretory wastes such as bacteria, which is equivalent to increasing the distance between the urethral stent (or urethra) and excretory wastes like urine bacteria, and carries antibacterial drugs in the contact space to make bacteria difficult to adhere; on the other hand, the flow of urine promotes peristaltic property of the villi-like structure and makes it less likely to adhere to bacteria and other substances, and finally it is eliminated from the body through the urethra; the silk fibroin film of the outer layer carries anti-stenosis drugs, after implantation, the drugs can be released slowly to the urethra (the drugs are carried in the silk fibroin film, and the silk fibroin has been proved as a natural tissue regeneration material matrix with good drug slow-release; the concentration, the crystallinity, and the regulation of secondary structure of the silk fibroin can carry different quantities and types of drugs, as well as achieve controllable release of the carried drugs), thus achieving the effect of treating inflammatory and traumatic urethral stenosis.

The following preferred technology program is presented to give a detailed description for this invention:

The said long-acting antibacterial anti-stenosis functional urethral stent, wherein a wall thickness of the long-acting antibacterial anti-stenosis functional urethral stent is 0.19-0.4 mm, and a wall thickness of the middle layer is 0.06-0.27 mm; wherein the length of the villus depends on the length of the molecular chain of the polymer containing polyhydroxy functional group, and the length of the microvillus depends on the length of the molecular chain of the polymer with antibacterial adhesion function; wherein the distribution density of the villus depends on the number of hydroxyl on the surface of chitosan, and the distribution density of the microvillus depends on the number of hydroxyl on the surface of villus.

The said long-acting antibacterial anti-stenosis functional urethral stent, wherein the fabric tube consists of yarns; wherein the yarn is one or more selected from the group consisting of silk, a polylactide (PLA, further divided into levorotatory PLLA and dextorotatory PLLA) filament, a polydiaxone (PDO) filament, a polyglycolide acid (PGA) filament, a poly(lactic-co-glycolic acid) (PLGA) filament and a developing wire (when using developing wire material, it can be developed under X-ray to locate the urethral stent), in order to guarantee good biocompatibility of the urethral stent and avoid immunological rejection of human body; it can be biodegraded in human body and doesn't need to be removed after implantation, reducing patient's second suffering;

through the tests performed according to the industrial standard of the People's Republic of China, YY/T 0872-2013, *"Test Methods for Urethral Stent"*, wherein the fabric tube has a radial compression modulus of 0.03-5.72 MPa, an elastic recovery ratio of 74.53-93.63%, a circumferential expansion breaking strength of 0.03-10.62 MPa, and a yarn coverage rate of 66.67-83.15%;

the urethral stent of this invention has excellent mechanical properties, can bear certain compressive and extensional deformation, and has good elastic recovery and bending resistance to ensure long-term patency and peristalsis of the urethral canal; excellent mechanical properties mainly depend on the fabric tube, but the fundamental reason is not only because the middle layer is a fabric tube, more because the composite stent has an overall combined effect, and specifications and types of raw materials, processing technology of fabric, specifications and parameters of fabric, and braided structure will affect the mechanical properties of the fabric; for example, the yarn can neither be too thick nor too thin, too thick yarn may lead to the excessive bending stiffness of bare stent of the middle fabric tube, and wall thickening and less lumen diameter of urethral stent of identical specification, which ultimately influences urination; too thin yarn may directly result in decreased properties of bare stent of the middle fabric tube such as compression modulus and elastic recovery ratio, inability to support diseased urethra, as well as susceptibility to displacement and separation, so that comprehensive consideration is required to make mechanical properties of the entire composite urethral stent reach an excellent level;

wherein the anti-stenosis drug is rapamycin and/or curcumin;

wherein the polymer containing polyhydroxy functional group is one or more selected from the group consisting of polyether, polyvinyl alcohol, polyethylene glycol, polyhydroxyethyl methacrylate and acrylic acid-hydroxypropyl acrylate copolymer;

wherein the polymer with antibacterial adhesion function is one or more selected from the group consisting of cationic polymer, anionic polymer, nonionic polymer and zwitterionic hydrophilic polymer;

wherein the antibacterial drug is one or more selected from the group consisting of antibacterial peptide, triclosan, heparin, clarithromycin, berberine, sparfloxacin, amikacin and ketolovic acid.

The said long-acting antibacterial anti-stenosis functional urethral stent, wherein the developing wire is a medical magnesium wire, a medical tantalum wire or a medical silver wire;

wherein the polymer with antibacterial adhesion function is one or more selected from the group consisting of polyvinylpyridine, phosphoylcholine polymer, sulphobetaine polymer, carboxybetaine polymer, polyethylene glycol and poly(2-methyl-2-oxazoline).

The invention also provides a method for preparing the long-acting antibacterial anti-stenosis functional urethral stent as described in any one of the above, comprising that, after making yarns into the fabric tube by textile molding, preparing the antibacterial and anti-fouling coating on the inner surface, and the silk fibroin film carrying anti-stenosis drugs on the outer surface respectively, to obtain the long-acting antibacterial anti-stenosis functional urethral stent;

wherein the steps for preparing the antibacterial antifouling coating are as follows:

(a) after coating the inner surface of the fabric tube with a nanosilica amino silicone oil modified epoxy resin mixed solution containing chitosan, drying at normal temperature, then baking and solidifying to form the chitosan-nanosilica array;

wherein the nanosilica amino silicone oil modified epoxy resin mixed solution containing chitosan is prepared by mixing a mixed solution containing nanosilica, a chitosan solution and a coupling agent and then performing ultrasonic dispersion;

wherein the mixed solution containing nanosilica is composed of nanosilica, amino silicon oil and epoxy resin;

(b) impregnating the product of step (a) in anhydrous toluene solution containing initiator to react at normal temperature, so that the initiator completely reacts with the —OH on the surface of chitosan molecule in the product of step (a), then rinsing with anhydrous toluene repeatedly to remove the excessive physically-absorbed initiator and other by-products, and then drying in a vacuum environment;

wherein the initiator is photoinitiator or halogen-containing initiator;

(c) sealing the product of step (b) in a tubular reactor, degassing and placing at a temperature of 20° C. and under the protection of nitrogen or inert gas, then injecting a polymeric solution into the tubular reactor until the product of step (b) is completely submerged and keeping for a period of time, during this process, the monomer in the polymeric solution and the initiation point on the inner surface of the fabric tube undergo an atom transfer radical polymerization reaction to form a villi structure;

wherein the polymeric solution is a solution containing monomer I, or a solution containing monomer I and a solution containing monomer II; wherein the monomer I and the monomer II are monomers corresponding to different types of polymers containing polyhydroxyl functional groups;

wherein the preparation process of the solution containing monomer I or the solution containing monomer II is: dissolving the monomer in methanol at a temperature of 20° C., after adding a catalyst, stirring and degassing under the protection of nitrogen or inert gas;

(d) after impregnating the product of step (c) in anhydrous toluene solution containing initiator to react at normal temperature, rinsing with anhydrous toluene repeatedly to remove the excessive physically-absorbed initiator and other by-products, then drying in a vacuum environment, during this process, the hydroxyl of the polymer on the surface of the villi is activated by the initiator;

wherein the initiator is photoinitiator or halogen-containing initiator;

(e) sealing the product of step (d) in the tubular reactor, degassing and placing at a temperature of 20° C. and under the protection of nitrogen or inert gas, then injecting the polymeric solution into the tubular reactor until the product of step (d) is completely submerged and keeping for a period of time, during this process, the monomer in the polymeric solution and the initiation point on the surface of the villi undergo an atom transfer radical polymerization reaction to form a microvilli structure;

wherein the polymeric solution is a solution containing monomer III, or a solution containing monomer III and a solution containing monomer IV; wherein the monomer III and the monomer IV are monomers corresponding to different types of polymers with antibacterial adhesion function;

wherein the preparation process of the solution containing monomer III or the solution containing monomer IV is: dissolving the monomer in methanol at a temperature of 20° C., then adding the catalyst, and stirring to degas under the protection of nitrogen or inert gas;

(f) washing the product of step (e) with deionized water and methanol repeatedly before drying, then impregnating in the antibacterial drug solution to form the antibacterial antifouling coating on the inner surface of the fabric tube.

The following preferred technology program is presented to give a detailed description for this invention:

The said method, wherein in step (a), the number of coating is 1-5 times, and the coating thickness of each time is 0.01-0.02 mm; the drying time at normal temperature is 0.5-3 h; the temperature of baking and solidifying is 80-100° C., and the time of baking and solidifying is 24-36 h; the volume ratio of the mixed solution containing nanosilica, the chitosan solution and the coupling agent is 2:2:1 or 2:1:1; the concentration of the chitosan solution is 1-10 wt %, which is prepared by adding chitosan to an acetic acid solution with a concentration of 0.5-1.5 wt %; the ultrasonic dispersion time is 1-3 h; in the mixed solution containing nanosilica, the content of nanosilica is 0.1-2.0 wt % and the content of amino silicon oil is 5-15 wt %;

wherein in step (b) or step (d), the initiator is trichlorosilane, 3-(trichlorosilyl)propyl-2-bromo-2-methylpropionate or ω-mercaptoundecyl bromoisobutyrate; the concentration of the initiator in the anhydrous toluene solution containing initiator is 5-7 mM; the reaction time is 10 h; the drying temperature is 50-100° C. and the drying time is 2-3 h;

wherein in step (c) or step (e), the period of time is 1-24 h; the content of monomer in the polymeric solution is 5-15 wt %; the catalyst is a mixture of copper bromide, cuprous bromide and 2,2-bipyridine with a mass ratio of 1:6:24, 1:3:12 or 1:2:8, and the mass ratio of catalyst to monomer is 2:25; the time of stirring and degassing is 15-20 min;

wherein in step (f), the concentration of the antibacterial drug solution is 0.1-5.0 mg/mL; the impregnating temperature is 25° C. and the impregnating time is 20-40 min.

The said method, wherein the preparation process of the silk fibroin film carrying anti-stenosis drugs is: using a coating brush to evenly coat the outer surface of the fabric tube with a mixed solution of silk fibroin carrying drugs for 1-5 times, with the coating thickness of 0.01-0.02 mm each time, forming the film by air-drying at a certain temperature, so that the film is uniform and completely covers outer surface of the fabric tube, then pre-cooling and freeze-drying successively to obtain the long-acting antibacterial anti-stenosis functional urethral stent; the temperature of pre-cooling is −80° C. and the time of pre-cooling is 3-24 h; the temperature of freeze-drying is (−80)-(−70° C.) and the time of freeze-drying is 48-72 h;

wherein the preparation process of the mixed solution of silk fibroin carrying drugs is: first, a silk fibroin solution with a concentration of 5-30 wt % and a polyethylene glycol solution with a concentration of 10-90 wt % are mixed in the mass ratio of 10:5 to obtain an intermediate mixed solution, and then a rapamycin solution with a concentration of 0.5-2.0 mg/mL and/or a curcumin solution with a concentration of 0.5-6.0 mg/mL are added to the intermediate mixed solution to obtain the mixed solution of silk fibroin carrying drugs, the volume ratio of the intermediate mixed solution to the rapamycin solution is 4:1, and the volume ratio of the intermediate mixed solution to the curcumin solution is 4:1.

The said method, when preparing the intermediate mixed solution, 5-70 wt % glycerin solution is also added, and the mass ratio of the polyethylene glycol solution to the glycerin solution is 5:3, 5:4 or 5:5.

The said method, wherein a steam treatment, an ultrasonic treatment or an ultraviolet irradiation is performed after forming the film by air-drying and before pre-cooling; the temperature of the steam treatment is 50-70° C. and the time of the steam treatment is 5-10 h; the time of the ultrasonic treatment is 30-300 min and the power of the ultrasonic treatment is 450-900 W; the time of the ultraviolet irradiation is 2-8 h and the power of the ultrasonic treatment is 15-30 W (i.e. the power of UV lamps).

The said method, wherein the textile molding uses one or more techniques selected from the group consisting of machine weaving, knitting and braiding.

The said method, wherein a pretreatment is performed after the fabric tube is prepared, that is, after washing the fabric tube with oxalic acid solution and distilled water successively to remove impurities like rust and oil stain, carrying out heat-setting of the fabric tube; when oxalic acid solution is used for washing, the concentration of oxalic acid solution is 1-15 wt %, the temperature of oxalic acid solution is 50-70° C., and the washing time is 30-60 min; when distilled water is used for washing with ultrasound, the number of washing is 2-5 times; the temperature of heat-setting depends on the material of the yarn, and is between the glass-transition temperature and the melting point, the time of heat-setting is 15-60 min.

Benefits:

The said urethral stent carrying antibacterial/anti-stenosis drugs of the invention has the following advantages:

(1) as the skeleton structure of the entire urethral stent, the middle fabric tube has good mechanical properties such as compression resistance, elastic recovery and bending resistance, ensuring mechanical support and drainage effect;

(2) the villi-like structure on the antibacterial antifouling coating on the surface of the stent not only avoids calcification of the inner lumen, deposition of carbonate and other wastes, and adhesion and growth of bacteria, but also increases the specific surface area of the lumen of the urethral stent and carries antibacterial drugs (the villi-like structure on one hand increases the contact space between the inner layer and excretory wastes such as bacteria, which is equivalent to increasing the distance between the urethral stent (or urethra) and excretory wastes like urine bacteria, and carries antibacterial drugs in the contact space to make bacteria difficult to adhere; on the other hand, the flow of urine promotes wriggling property of the villi-like structure and makes it less likely to adhere to bacteria and other substances, and finally it is eliminated from the body through the urethra); the silk fibroin film of the outer layer carries anti-stenosis drugs, after implantation, the drugs can be released slowly to the urethra (the drugs are carried in the silk fibroin film, and the silk fibroin has been proved as a natural tissue regeneration material matrix with good drug slow-release; the concentration, the crystallinity, and the regulation of secondary structure of the silk fibroin can carry different quantities and types of drugs, as well as achieve controllable release of the carried drugs), thus achieving the effect of treating inflammatory and traumatic urethral stenosis;

(3) the urethral stent of the invention, after implanting in the human urethra, can inhibit the formation of stenosis, and can also inhibit excessive growth of fibroblast and excessive deposition of collagen tissue to a certain degree;

(4) the urethral stent has good biocompatibility and safety, and reduces the generation of macrophages and inflammatory factors;

(5) the selection of different materials and modification methods (the steam treatment, the glycerin treatment, the ultrasonic treatment, the ultraviolet irradiation and etc.) can regulate the degradation rate of the urethral stent, thus maintaining normal urination function of the urethra during the drug slow-release treatment of stenosis.

DETAILED DESCRIPTION OF THE EMBODIMENTS

Figure 1:
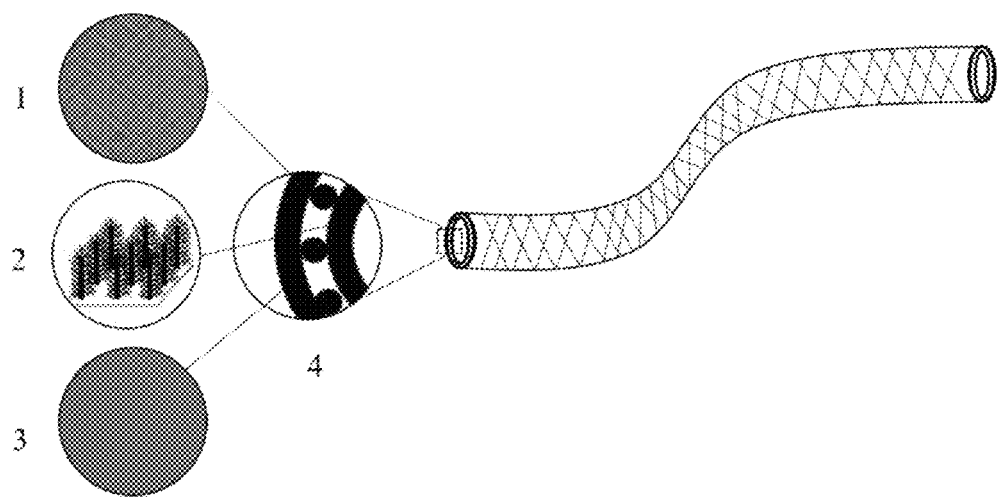
FIG. 1 is a schematic structural diagram of the long-acting antibacterial anti-stenosis functional urethral stent prepared by Example 1, wherein 1 refers to the fabric tube, 2 refers to the antibacterial antifouling coating, 3 refers to the silk fibroin film carrying anti-stenosis drugs (rapamycin and curcumin)

Based on above mentioned method, the following embodiments are carried out for further demonstration in the present invention. It is to be understood that these embodiments are only intended to illustrate the invention and are not intended to limit the scope of the invention. In addition, it should be understood that after reading the contents described in the present invention, those technical personnel in this field can make various changes or modifications to the invention, and these equivalent forms also fall within the scope of the claims attached to the application.

The test method of radial compression modulus, elastic recovery ratio, circumferential expansion breaking strength and yarn coverage rate of the fabric tube: testing with reference to the industrial standard of the People's Republic of China, YY/T 0872-2013, *"Test Methods for Urethral Stent"*.

The test method of antibacterial antifouling ability of the long-acting antibacterial anti-stenosis functional urethral stent: choosing *Escherichia coli* of Gram-negative bacteria as the test strain, and evaluating according to the antibacterial activity, the evaluation standard is ISO 20645:2004.

The test steps for the release time and cumulative release rate of anti-stenosis drugs on the outer layer of the long-acting antibacterial anti-stenosis functional urethral stent are as follows:

(1) preparing a drug solution at a certain concentration gradient, then using ultraviolet spectrophotometer to measure its absorbance, drawing the standard curve of the drug with the absorbance as the x axis and the concentration as the y axis;

(2) weighing the anti-stenosis drug into a centrifuge tube, adding PBS buffer (pH=7.4, 10 mM) and mixing well, then placing the centrifuge tube on a oscillator in a 37° C. oven (frequency is 100 rad/min);

(3) extracting the release solution at the set appropriate time points (0, 3 h, 6 h, 12 h, 24 h, 36 h, 48 h, 72 h, 96 h, 120 h, 168 h, 240 h, 360 h, 400 h), then re-adding fresh PBS buffer to the centrifuge tube, and placing the tube back on the oscillator in the 37° C. oven; measuring the absorbance (OD value) with ultraviolet-visible spectrophotometer, obtaining the drug release concentration through the standard curve, then calculating the cumulative release rate according to the following formula:

$$\text{Cumulative release rate (\%)} = \frac{C_n \times V_0 + (C_1 + C_2 + \ldots + C_{n-1}) \times V}{W_0};$$

in the formula: $C_n$ is the concentration of the nth sampling point; $V_0$ is the volume of the release medium; V is the volume of each sampling; $W_0$ is the drug capacity of the sample.

Example 1

A method of preparing the long-acting antibacterial anti-stenosis functional urethral stent, comprises the following steps:
(1) Preparation of Fabric Tube;
  making yarns into the fabric tube by textile molding, wherein the yarn is composed of multiple silk filaments with a fineness of 7 tex and a medical magnesium wire with developing function with a fineness of 7 tex; wherein the textile molding uses the braiding technique, the machine is an automatic 8-spindle braiding machine, the braiding structure is diamond braid (1/1 interweave), the braiding speed is 40 rpm, the gear ratio is 82/21, and the braiding height is 25 cm;
  the prepared fabric tube is a fabric with tubular structure, and the fabric tube has a radial compression modulus of 0.03 MPa, an elastic recovery ratio of 74.68%, a circumferential expansion breaking strength of 0.03 MPa, and a yarn coverage rate of 67.11%;
(2) Pretreatment;
  first, washing the fabric tube prepared in step (1) with an oxalic acid solution with a concentration of 1 wt % at 50° C. for 30 min, then washing the fabric tube with distilled water twice with ultrasound before heat-setting, the temperature of heat-setting is 100° C., and the time of heat-setting is 20 min;
(3) Preparation of Antibacterial Antifouling Coating;
  (a) after coating the inner surface of the fabric tube with a nanosilica amino silicone oil modified epoxy resin mixed solution containing chitosan for 1 time (the coating thickness is 0.01 mm), drying at normal temperature for 0.5 h, then baking and solidifying at 80° C. for 24 h to form the chitosan-nanosilica array;
  the nanosilica amino silicone oil modified epoxy resin mixed solution containing chitosan is prepared by mixing the mixed solution containing nanosilica, the chitosan solution and the silane coupling agent YDH-660 in a volume ratio of 2:2:1, then performing ultrasonic dispersion for 3 h;
  the mixed solution containing nanosilica is composed of 0.1 wt % nanosilica, 5 wt % amino silicon oil and an appropriate amount of epoxy resin;
  the concentration of the chitosan solution is 1 wt %, which is prepared by adding chitosan to an acetic acid solution with a concentration of 0.5 wt %;
  (b) after impregnating the product of step (a) in anhydrous toluene solution containing initiator (the concentration of the initiator is 5 mM, and the initiator is ω-mercaptoundecyl bromoisobutyrate) to react at normal temperature for 10 h, rinsing with anhydrous toluene, then drying at 50° C. in a vacuum environment (vacuum degree is 0.09 MPa) for 3 h;
  (c) sealing the product of step (b) in a tubular reactor, degassing and placing at a temperature of 20° C. and under the protection of nitrogen, then injecting a polymeric solution into the tubular reactor until the product of step (b) is completely submerged and keeping for 15 h;
  the polymeric solution is a solution containing the mixture of acrylic acid and hydroxypropyl acrylate; the content of the mixture of acrylic acid and hydroxypropyl acrylate in the polymeric solution is 5 wt %;
  the preparation process of the solution containing the mixture of acrylic acid and hydroxypropyl acrylate is: dissolving the mixture of acrylic acid and hydroxypropyl acrylate (mass ratio as 1:1) in methanol at 20° C., after adding the catalyst, stirring and degassing under the protection of nitrogen for 15 min; the catalyst is a mixture of copper bromide, cuprous bromide and 2,2-bipyridine with a mass ratio of 1:6:24, and the mass ratio of the catalyst to the mixture of acrylic acid and hydroxypropyl acrylate is 2:25;
  (d) after impregnating the product of step (c) in anhydrous toluene solution containing initiator (the concentration of the initiator is 5 mM, and the initiator is ω-mercaptoundecyl bromoisobutyrate) to react at normal temperature for 10 h, rinsing with anhydrous toluene, then drying at 50° C. in a vacuum environment (vacuum degree is 0.09 MPa) for 3 h;
  (e) sealing the product of step (d) in a tubular reactor, degassing and placing at a temperature of 20° C. and under the protection of nitrogen, then injecting a polymeric solution into the tubular reactor until the product of step (d) is completely submerged and keeping for 15 h;
  the polymeric solution is a solution containing sulfobetaine methacrylic acid, and the content of the sulfobetaine methacrylic acid in the polymeric solution is 5 wt %;
  the preparation process of the solution containing sulfobetaine methacrylic acid is: dissolving sulfobetaine methacrylic acid in methanol at 20° C., after adding the catalyst, stirring and degassing under the protection of nitrogen for 15 min; the catalyst is a mixture of copper bromide, cuprous bromide and 2,2-bipyridine with a mass ratio of 1:6:24, and the mass ratio of the catalyst to sulfobetaine methacrylic acid is 2:25;
  (f) washing the product of step (e) with deionized water and methanol before drying, then impregnating in a triclosan solution with a concentration of 0.1 mg/mL at 25° C. for 20 min to form the antibacterial antifouling coating on the inner surface of the fabric tube;
(4) Preparation of the Silk Fibroin Film Carrying Rapamycin and Curcumin;
  using the coating brush to evenly coat the outer surface of the fabric tube with the mixed solution of silk fibroin carrying drugs for 1 time, with the coating thickness of 0.02 mm, forming the film by air-drying at 25° C., then carrying out the steam treatment (at 50° C. for 10 h), pre-cooling (at −80° C. for 3 h) and freeze-drying (at −70° C. for 72 h) successively to obtain the long-acting antibacterial anti-stenosis functional urethral stent;
  the preparation process of the mixed solution of silk fibroin carrying drugs is: first, a silk fibroin solution with a concentration of 15 wt %, a polyethylene glycol solution with a concentration of 10 wt %, and a glycerin solution with a concentration of 5 wt % are mixed in the mass ratio of 10:5:3 to obtain an intermediate mixed solution, and then a rapamycin solution with a concentration of 0.5 mg/mL and a curcumin solution with a concentration of 0.5 mg/ml are added to the intermediate mixed solution to obtain the mixed solution of silk fibroin carrying drugs, the volume ratio of the intermediate mixed solution to the rapamycin solution is 4:1, and the volume ratio of the intermediate mixed solution to the curcumin solution is 4:1.

Figure 2:
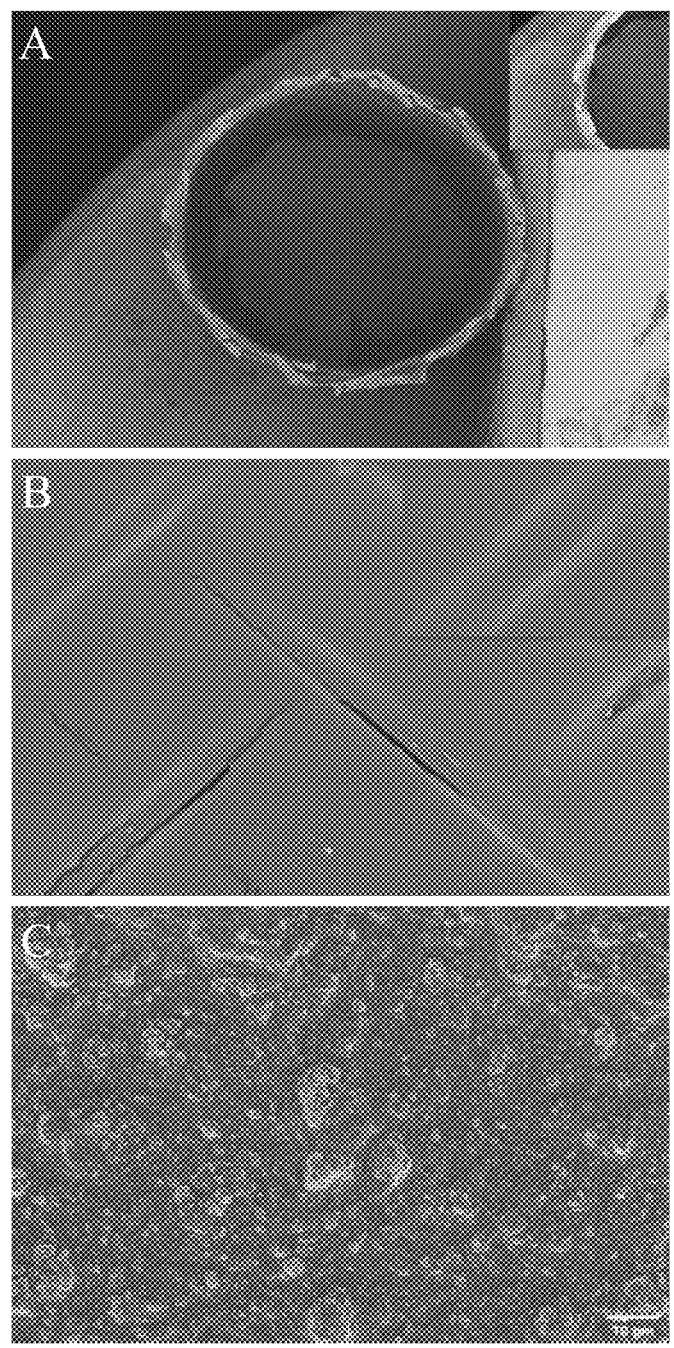
FIG. 2 is an SEM diagram of the long-acting antibacterial anti-stenosis functional urethral stent prepared by Example 1, wherein A refers to a cross-sectional view of the urethral stent, B refers to a planar graph of the silk fibroin film carrying anti-stenosis drugs (rapamycin and curcumin), C refers to a planar graph of the antibacterial antifouling coating.

The prepared long-acting antibacterial anti-stenosis functional urethral stent is a tubular structure, as shown in FIGS. 1-2, consisting of three layers: inner, middle and outer layers; the middle layer is the fabric tube 1; the outer layer is the silk fibroin film 3 carrying rapamycin and curcumin; the inner layer is the antibacterial antifouling coating 2, consisting of chitosan-nanosilica arrays, villi, microvilli and triclosan; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is acrylic acid-hydroxypropyl acrylate copolymer, which is bonded with the chitosan in the chitosan-nanosilica array through covalent bonds; one end of the microvillus is fixed to the villus while the other end is a free end, and the material of the microvillus is polymethacrylate sulfobetaine, which is bonded with the villus through covalent bonds; the triclosan is distributed in the whole inner layer; the wall thickness of the long-acting antibacterial anti-stenosis functional urethral stent is 0.21 mm, and the wall thickness of the middle layer is 0.18 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 89.47%.

Example 2

A method of preparing the long-acting antibacterial anti-stenosis functional urethral stent, comprises the following steps:
(1) Preparation of Fabric Tube;
  making yarns into the fabric tube by textile molding, wherein the yarn is composed of multiple polylactide filaments with a fineness of 20 tex and a medical tantalum wire with developing function with a fineness of 20 tex; wherein the textile molding uses the knitting technique, and the knitting structure is weft-knitting single jersey;
  the prepared fabric tube is a fabric with tubular structure, with the transverse coil density as 25 rows/5 cm, the longitudinal coil density as 25 columns/5 cm, the coil length as 5 mm, and total density as 2000 coils/25 $cm^2$; the fabric tube has a radial compression modulus of 1.31 MPa, an elastic recovery ratio of 87.14%, a circumferential expansion breaking strength of 4.88 MPa, and a yarn coverage rate of 75.32%;
(2) Pretreatment;
  first, washing the fabric tube prepared in step (1) with an oxalic acid solution with a concentration of 2 wt % at 52° C. for 35 min, then washing the fabric tube with distilled water twice with ultrasound before heat-setting, the temperature of heat-setting is 80° C., and the time of heat-setting is 15 min;
(3) Preparation of Antibacterial Antifouling Coating;
  (a) after coating the inner surface of the fabric tube with a nanosilica amino silicone oil modified epoxy resin mixed solution containing chitosan for 2 times (the coating thickness of each time is 0.02 mm), drying at normal temperature for 1 h, then baking and solidifying at 85° C. for 26 h to form the chitosan-nanosilica array;
  the nanosilica amino silicone oil modified epoxy resin mixed solution containing chitosan is prepared by mixing the mixed solution containing nanosilica, the chitosan solution and the silane coupling agent YDH-660 in a volume ratio of 2:1:1, then performing ultrasonic dispersion for 2 h;
  the mixed solution containing nanosilica is composed of 0.5 wt % nanosilica, 8 wt % amino silicon oil and an appropriate amount of epoxy resin;
  the concentration of the chitosan solution is 3 wt %, which is prepared by adding chitosan to an acetic acid solution with a concentration of 0.7 wt %;
  (b) after impregnating the product of step (a) in anhydrous toluene solution containing initiator (the concentration of the initiator is 6 mM, and the initiator is 3-(trichlorosilyl)propyl-2-bromo-2-methylpropionate) to react at normal temperature for 10 h, rinsing with anhydrous toluene, then drying at 60° C. in a vacuum environment (vacuum degree is 0.09 MPa) for 2.5 h;
  (c) sealing the product of step (b) in a tubular reactor, degassing and placing at a temperature of 20° C. and under the protection of nitrogen, then injecting a polymeric solution into the tubular reactor until the product of step (b) is completely submerged and keeping for 1 h;
  the polymeric solution is a solution containing hydroxyethyl methacrylate; the content of hydroxyethyl methacrylate in the polymeric solution is 7 wt %;
  the preparation process of the solution containing hydroxyethyl methacrylate is: dissolving hydroxyethyl methacrylate in methanol at 20° C., after adding the catalyst, stirring and degassing under the protection of nitrogen for 16 min; the catalyst is a mixture of copper bromide, cuprous bromide and 2,2-bipyridine with a mass ratio of 1:3:12, and the mass ratio of the catalyst to hydroxyethyl methacrylate is 2:25;
  (d) after impregnating the product of step (c) in anhydrous toluene solution containing initiator (the concentration of the initiator is 6 mM, and the initiator is 3-(trichlorosilyl)propyl-2-bromo-2-methylpropionate) to react at normal temperature for 10 h, rinsing with anhydrous toluene, then drying at 60° C. in a vacuum environment (vacuum degree is 0.09 MPa) for 2.5 h;
  (e) sealing the product of step (d) in a tubular reactor, degassing and placing at a temperature of 20° C. and under the protection of nitrogen, then injecting a polymeric solution into the tubular reactor until the product of step (d) is completely submerged and keeping for 1 h;
  the polymeric solution is a solution containing vinylpyridine and a solution containing ethylene glycol with a mass ratio of 1:1; the content of vinylpyridine in the solution containing vinylpyridine is 7 wt %; the content of ethylene glycol in the solution containing ethylene glycol is 7 wt %;
  the preparation process of the solution containing vinylpyridine is: dissolving vinylpyridine in methanol at 20° C., after adding the catalyst, stirring and degassing under the protection of nitrogen for 16 min;
  the preparation process of the solution containing ethylene glycol is: dissolving ethylene glycol in methanol at 20° C., after adding the catalyst, stirring and degassing under the protection of nitrogen for 16 min;
  the catalyst is a mixture of copper bromide, cuprous bromide and 2,2-bipyridine with a mass ratio of 1:3:12; the mass ratio of the catalyst to vinylpyridine is 2:25; the mass ratio of the catalyst to ethylene glycol is 2:25;

(f) washing the product of step (e) with deionized water and methanol before drying, then impregnating in a heparin solution with a concentration of 0.5 mg/mL at 25° C. for 25 min to form the antibacterial antifouling coating on the inner surface of the fabric tube;

(4) Preparation of the Silk Fibroin Film Carrying Rapamycin;

using the coating brush to evenly coat the outer surface of the fabric tube with the mixed solution of silk fibroin carrying drugs for 2 times, with the coating thickness of 0.02 mm each time, forming the film by air-drying at 60° C., then carrying out the steam treatment (at 53° C. for 9 h), pre-cooling (at −80° C. for 5 h) and freeze-drying (at −72° C. for 65 h) successively to obtain the long-acting antibacterial anti-stenosis functional urethral stent;

the preparation process of the mixed solution of silk fibroin carrying drugs is: first, a silk fibroin solution with a concentration of 8 wt %, a polyethylene glycol solution with a concentration of 15 wt %, and a glycerin solution with a concentration of 10 wt % are mixed in the mass ratio of 10:5:4 to obtain an intermediate mixed solution, and then a rapamycin solution with a concentration of 0.5 mg/mL is added to the intermediate mixed solution to obtain the mixed solution of silk fibroin carrying drugs, and the volume ratio of the intermediate mixed solution to the rapamycin solution is 4:1.

Figure 3:
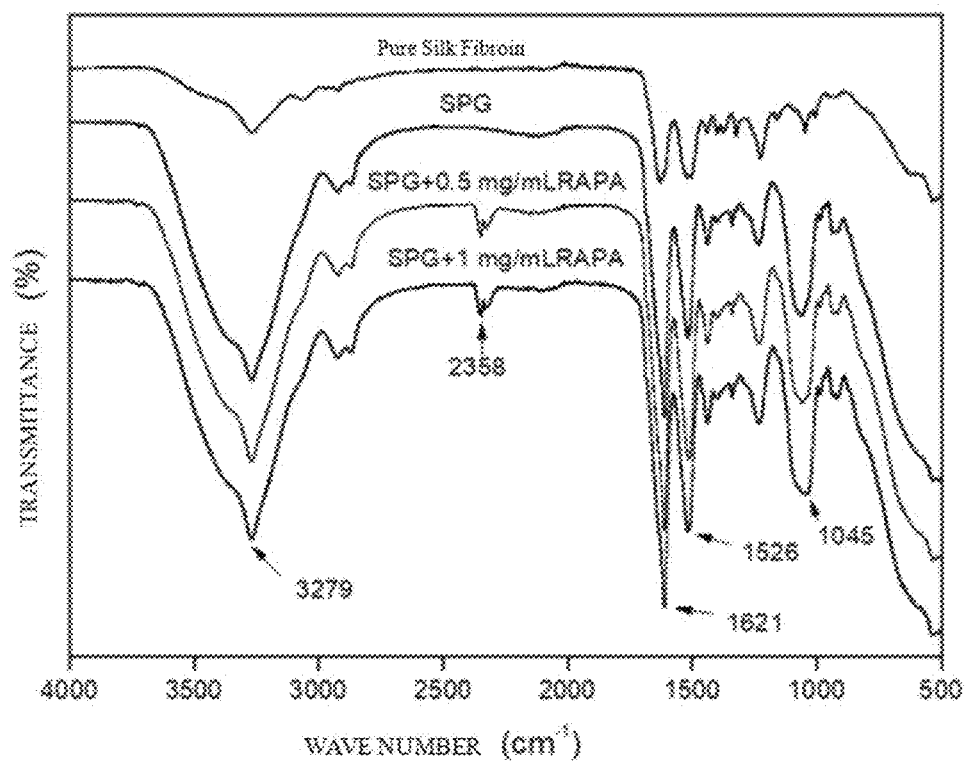
FIG. 3 is an infrared spectrum of the silk fibroin film carrying anti-stenosis drugs in the long-acting antibacterial anti-stenosis functional urethral stent prepared by Example 2, wherein SPG represents a mixture of silk fibroin, polyethylene glycol, and glycerol, and RAPA represents the drug rapamycin.

The prepared long-acting antibacterial anti-stenosis functional urethral stent is a tubular structure, consisting of three layers: inner, middle and outer layers; the middle layer is the fabric tube; the outer layer is the silk fibroin film carrying rapamycin, FIG. 3 is the infrared spectrogram of the silk fibroin film carrying rapamycin in the long-acting antibacterial anti-stenosis functional urethral stent prepared by Example 2, detects the changes of characteristic peaks before and after carrying the drug onto the urethral stent, showing that rapamycin is successfully carried onto the silk fibroin film without chemical reaction; the inner layer is the antibacterial antifouling coating, consisting of chitosan-nanosilica arrays, villi, microvilli and heparin; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyhydroxyethyl methacrylate, which is bonded with the chitosan in the chitosan-nanosilica array through covalent bonds; one end of the microvillus is fixed to the villus while the other end is a free end, and the material of the microvillus is a mixture of polyvinylpyridine and polyethylene glycol, which is bonded with the villus through covalent bonds; the heparin is distributed in the whole inner layer; the wall thickness of the long-acting antibacterial anti-stenosis functional urethral stent is 0.35 mm, and the wall thickness of the middle layer is 0.27 mm; the antibacterial antifouling ability of the long-acting antibacterial anti-stenosis functional urethral stent can last until the 4th day, the width of the antibacterial zone is 0.34 mm, the slow-release time of anti-stenosis drugs on the outer layer can reach 400 hours, and the cumulative release rate of the drug is 80.63%.

Example 3

A method of preparing the long-acting antibacterial anti-stenosis functional urethral stent, comprises the following steps:

(1) Preparation of Fabric Tube;

making yarns into the fabric tube by textile molding, wherein the yarn is composed of multiple polydiaxone filaments with a fineness of 40 tex and a medical silver wire with developing function with a fineness of 40 tex; wherein the textile molding uses the machine weaving technique, and the machine weaving structure is plain weave;

the prepared fabric tube is a fabric with tubular structure, with the warp density as 100 pieces/10 cm, and the weft density as 100 pieces/10 cm; the fabric tube has a radial compression modulus of 2.11 MPa, an elastic recovery ratio of 81.57%, a circumferential expansion breaking strength of 5.79 MPa, and a yarn coverage rate of 66.67%;

(2) Pretreatment;

first, washing the fabric tube prepared in step (1) with an oxalic acid solution with a concentration of 4 wt % at 55° C. for 40 min, then washing the fabric tube with distilled water 3 times with ultrasound before heat-setting, the temperature of heat-setting is 85° C., and the time of heat-setting is 30 min;

(3) Preparation of Antibacterial Antifouling Coating;

(a) after coating the inner surface of the fabric tube with a nanosilica amino silicone oil modified epoxy resin mixed solution containing chitosan for 3 times (the coating thickness of each time is 0.01 mm), drying at normal temperature for 1.5 h, then baking and solidifying at 90° C. for 28 h to form the chitosan-nanosilica array;

the nanosilica amino silicone oil modified epoxy resin mixed solution containing chitosan is prepared by mixing the mixed solution containing nanosilica, the chitosan solution and the silane coupling agent YDH-660 in a volume ratio of 2:1:1, then performing ultrasonic dispersion for 2.5 h;

the mixed solution containing nanosilica is composed of 0.8 wt % nanosilica, 10 wt % amino silicon oil and an appropriate amount of epoxy resin;

the concentration of the chitosan solution is 4 wt %, which is prepared by adding chitosan to an acetic acid solution with a concentration of 0.9 wt %;

(b) after impregnating the product of step (a) in anhydrous toluene solution containing initiator (the concentration of the initiator is 7 mM, and the initiator is trichlorosilane) to react at normal temperature for 10 h, rinsing with anhydrous toluene, then drying at 70° C. in a vacuum environment (vacuum degree is 0.09 MPa) for 2.7 h;

(c) sealing the product of step (b) in a tubular reactor, degassing and placing at a temperature of 20° C. and under the protection of nitrogen, then injecting a polymeric solution into the tubular reactor until the product of step (b) is completely submerged and keeping for 4 h;

the polymeric solution is a solution containing vinyl alcohol; the content of vinyl alcohol in the polymeric solution is 9 wt %;

the preparation process of the solution containing vinyl alcohol is: dissolving vinyl alcohol in methanol at 20° C., after adding the catalyst, stirring and degassing under the protection of nitrogen for 20 min; the catalyst is a mixture of copper bromide, cuprous bromide and 2,2-bipyridine with a mass ratio of 1:2:8, and the mass ratio of the catalyst to vinyl alcohol is 2:25;

(d) after impregnating the product of step (c) in anhydrous toluene solution containing initiator (the concentration of the initiator is 7 mM, and the initiator is 3-(trichlorosilyl)propyl-2-bromo-2-methylpropionate) to react at normal temperature for 10 h, rinsing with anhydrous toluene, then drying at 70° C. in a vacuum environment (vacuum degree is 0.09 MPa) for 2.7 h;

(e) sealing the product of step (d) in a tubular reactor, degassing and placing at a temperature of 20° C. and under the protection of nitrogen, then injecting a polymeric solution into the tubular reactor until the product of step (d) is completely submerged and keeping for 4 h;

the polymeric solution is a solution containing 2-methyl-2-oxazoline; the content of 2-methyl-2-oxazoline in the polymeric solution is 9 wt %;

the preparation process of the solution containing 2-methyl-2-oxazoline is: dissolving 2-methyl-2-oxazoline in methanol at 20° C., after adding the catalyst, stirring and degassing under the protection of nitrogen for 20 min; the catalyst is a mixture of copper bromide, cuprous bromide and 2,2-bipyridine with a mass ratio of 1:2:8, and the mass ratio of the catalyst to 2-methyl-2-oxazoline is 2:25;

(f) washing the product of step (e) with deionized water and methanol before drying, then impregnating in a berberine solution with a concentration of 1 mg/mL at 25° C. for 30 min to form the antibacterial antifouling coating on the inner surface of the fabric tube;

(4) Preparation of the Silk Fibroin Film Carrying Curcumin;

using the coating brush to evenly coat the outer surface of the fabric tube with the mixed solution of silk fibroin carrying drugs for 3 times, with the coating thickness of 0.01 mm each time, forming the film by air-drying at 4° C., then carrying out the steam treatment (at 55° C. for 8 h), pre-cooling (at −80° C. for 8 h) and freeze-drying (at −74° C. for 62 h) successively to obtain the long-acting antibacterial anti-stenosis functional urethral stent;

the preparation process of the mixed solution of silk fibroin carrying drugs is: first, a silk fibroin solution with a concentration of 10 wt %, a polyethylene glycol solution with a concentration of 20 wt %, and a glycerin solution with a concentration of 15 wt % are mixed in the mass ratio of 10:5:5 to obtain an intermediate mixed solution, and then a curcumin solution with a concentration of 0.8 mg/mL is added to the intermediate mixed solution to obtain the mixed solution of silk fibroin carrying drugs, and the volume ratio of the intermediate mixed solution to the curcumin solution is 4:1.

The prepared long-acting antibacterial anti-stenosis functional urethral stent is a tubular structure, consisting of three layers: inner, middle and outer layers; the middle layer is the fabric tube; the outer layer is the silk fibroin film carrying curcumin; the inner layer is the antibacterial antifouling coating, consisting of chitosan-nanosilica arrays, villi, microvilli and berberine; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyvinyl alcohol, which is bonded with the chitosan in the chitosan-nanosilica array through covalent bonds; one end of the microvillus is fixed to the villus while the other end is a free end, and the material of the microvillus is poly(2-methyl-2-oxazoline), which is bonded with the villus through covalent bonds; the berberine is distributed in the whole inner layer; the wall thickness of the long-acting antibacterial anti-stenosis functional urethral stent is 0.20 mm, and the wall thickness of the middle layer is 0.14 mm; the antibacterial antifouling ability of the long-acting antibacterial anti-stenosis functional urethral stent can last until the 4th day, the width of the antibacterial zone is 0.76 mm, the slow-release time of anti-stenosis drugs on the outer layer can reach 400 hours, and the cumulative release rate of the drug is 63.25%.

Example 4

A method of preparing the long-acting antibacterial anti-stenosis functional urethral stent, basically is the same as in Example 3, except that there is no steam treatment after freeze-drying in step (4).

Figure 6:
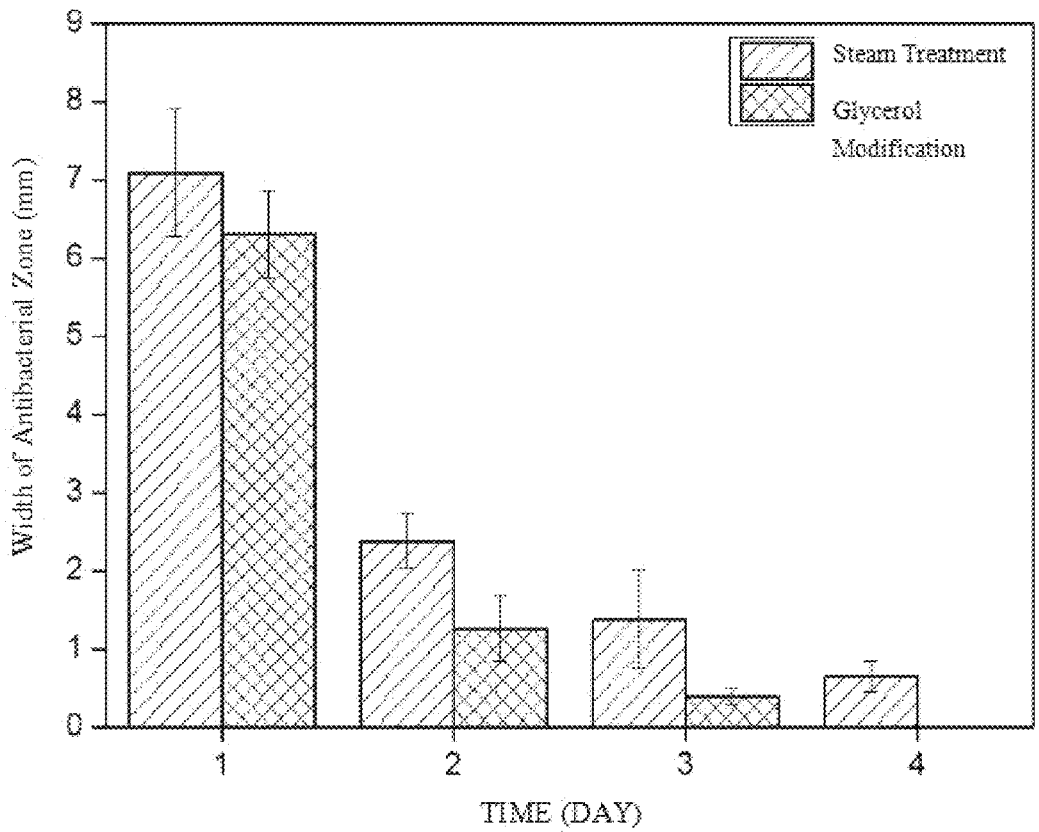
FIG. 6 is a graph of the sustained antibacterial property of the antibacterial antifouling coating in the long-acting antibacterial anti-stenosis functional urethral stent prepared in Examples 4-5 against *Escherichia coli* after different treatments.

The prepared long-acting antibacterial anti-stenosis functional urethral stent is a tubular structure, consisting of three layers: inner, middle and outer layers; the middle layer is the fabric tube; the outer layer is the silk fibroin film carrying curcumin; the inner layer is the antibacterial antifouling coating, consisting of chitosan-nanosilica arrays, villi, microvilli and berberine; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyvinyl alcohol, which is bonded with the chitosan in the chitosan-nanosilica array through covalent bonds; one end of the microvillus is fixed to the villus while the other end is a free end, and the material of the microvillus is poly(2-methyl-2-oxazoline), which is bonded with the villus through covalent bonds; the berberine is distributed in the whole inner layer; as shown in FIG. 6, the wall thickness of the long-acting antibacterial anti-stenosis functional urethral stent is 0.20 mm, and the wall thickness of the middle layer is 0.14 mm; the antibacterial antifouling ability of the long-acting antibacterial anti-stenosis functional urethral stent can last until the 3rd day, the width of the antibacterial zone is 0.39 mm, the slow-release time of anti-stenosis drugs on the outer layer can reach 400 hours, and the cumulative release rate of the drug is 59.60%.

Example 5

A method of preparing the long-acting antibacterial anti-stenosis functional urethral stent, basically is the same as in Example 3, except that there is no glycerin solution added in the preparation process of the mixed solution of silk fibroin carrying drugs in step (4).

The prepared long-acting antibacterial anti-stenosis functional urethral stent is a tubular structure, consisting of three layers: inner, middle and outer layers; the middle layer is the fabric tube; the outer layer is the silk fibroin film carrying curcumin; the inner layer is the antibacterial antifouling coating, consisting of chitosan-nanosilica arrays, villi, microvilli and berberine; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyvinyl alcohol, which is bonded with the chitosan in the chitosan-nanosilica array through covalent bonds; one end of the microvillus is fixed to the villus while the other end is a free end, and the material of the microvillus is poly(2-methyl-2-oxazoline), which is bonded with the villus through covalent bonds; the berberine is distributed in the whole inner layer; the wall thickness of the long-acting antibacterial anti-stenosis functional urethral stent is 0.20 mm, and the wall thickness of the middle layer is 0.14 mm;

as shown in FIG. 6, the antibacterial antifouling ability of the long-acting antibacterial anti-stenosis functional urethral stent can last until the 4th day, the width of the antibacterial zone is 0.64 mm, the slow-release time of anti-stenosis drugs on the outer layer can reach 400 hours, and the cumulative release rate of the drug is 61.51%.

Example 6

A method of preparing the long-acting antibacterial anti-stenosis functional urethral stent, comprises the following steps:

(1) Preparation of Fabric Tube;
- making yarns into the fabric tube by textile molding, wherein the yarn is composed of multiple polyglycolide acid filaments with a fineness of 70 tex and a medical silver wire with developing function with a fineness of 70 tex; wherein the textile molding uses the braiding technique, the machine is an automatic 16-spindle braiding machine, the braiding structure is regular braid (2/2 interweave), the braiding speed is 50 rpm, the gear ratio is 82/44, and the braiding height is 30 cm;
- the prepared fabric tube is a fabric with tubular structure, and the fabric tube has a radial compression modulus of 0.78 MPa, an elastic recovery ratio of 87.91%, a circumferential expansion breaking strength of 0.43 MPa, and a yarn coverage rate of 81.52%;

(2) Pretreatment;
first, washing the fabric tube prepared in step (1) with an oxalic acid solution with a concentration of 7 wt % at 60° C. for 50 min, then washing the fabric tube with distilled water 4 times with ultrasound before heat-setting, the temperature of heat-setting is 95° C., and the time of heat-setting is 40 min;

(3) Preparation of Antibacterial Antifouling Coating;
- (a) after coating the inner surface of the fabric tube with a nanosilica amino silicone oil modified epoxy resin mixed solution containing chitosan for 4 times (the coating thickness of each time is 0.01 mm), drying at normal temperature for 2 h, then baking and solidifying at 100° C. for 30 h to form the chitosan-nanosilica array;
- the nanosilica amino silicone oil modified epoxy resin mixed solution containing chitosan is prepared by mixing the mixed solution containing nanosilica, the chitosan solution and the silane coupling agent YDH-660 in a volume ratio of 2:1:1, then performing ultrasonic dispersion for 3 h;
- the mixed solution containing nanosilica is composed of 1.2 wt % nanosilica, 15 wt % amino silicon oil and an appropriate amount of epoxy resin;
- the concentration of the chitosan solution is 7 wt %, which is prepared by adding chitosan to an acetic acid solution with a concentration of 1.1 wt %;
- (b) after impregnating the product of step (a) in anhydrous toluene solution containing initiator (the concentration of the initiator is 7 mM, and the initiator is trichlorosilane) to react at normal temperature for 10 h, rinsing with anhydrous toluene, then drying at 80° C. in a vacuum environment (vacuum degree is 0.09 MPa) for 3 h;
- (c) sealing the product of step (b) in a tubular reactor, degassing and placing at a temperature of 20° C. and under the protection of neon, then injecting a polymeric solution into the tubular reactor until the product of step (b) is completely submerged and keeping for 10 h;
- the polymeric solution is a solution containing ethylene glycol; the content of ethylene glycol in the polymeric solution is 12 wt %;
- the preparation process of the solution containing ethylene glycol is: dissolving ethylene glycol in methanol at 20° C., after adding the catalyst, stirring and degassing under the protection of neon for 20 min; the catalyst is a mixture of copper bromide, cuprous bromide and 2,2-bipyridine with a mass ratio of 1:2:8, and the mass ratio of the catalyst to ethylene glycol is 2:25;
- (d) after impregnating the product of step (c) in anhydrous toluene solution containing initiator (the concentration of the initiator is 7 mM, and the initiator is trichlorosilane) to react at normal temperature for 10 h, rinsing with anhydrous toluene, then drying at 80° C. in a vacuum environment (vacuum degree is 0.09 MPa) for 3 h;
- (e) sealing the product of step (d) in a tubular reactor, degassing and placing at a temperature of 20° C. and under the protection of neon, then injecting a polymeric solution into the tubular reactor until the product of step (d) is completely submerged and keeping for 10 h;
- the polymeric solution is a solution containing 2-methacryloyloxyethyl phosphorylcholine; the content of 2-methacryloyloxyethyl phosphorylcholine in the polymeric solution is 12 wt %;
- the preparation process solution containing 2-methacryloyloxyethyl phosphorylcholine is: dissolving 2-methacryloyloxyethyl phosphorylcholine in methanol at 20° C., after adding the catalyst, stirring and degassing under the protection of neon for 20 min; the catalyst is a mixture of copper bromide, cuprous bromide and 2,2-bipyridine with a mass ratio of 1:2:8, and the mass ratio of the catalyst to 2-methacryloyloxyethyl phosphorylcholine is 2:25;
- (f) washing the product of step (e) with deionized water and methanol before drying, then impregnating in a antibacterial peptide solution with a concentration of 2 mg/mL at 25° C. for 40 min to form the antibacterial antifouling coating on the inner surface of the fabric tube;

(4) preparation of the silk fibroin film carrying rapamycin and curcumin;
- using the coating brush to evenly coat the outer surface of the fabric tube with the mixed solution of silk fibroin carrying drugs for 5 times, with the coating thickness of 0.01 mm each time, forming the film by air-drying at 4° C., then carrying out the ultrasonic treatment (power 450 W for 60 min), pre-cooling (at −80° C. for 16 h) and freeze-drying (at −78° C. for 50 h) successively to obtain the long-acting antibacterial anti-stenosis functional urethral stent;
- the preparation process of the mixed solution of silk fibroin carrying drugs is: first, a silk fibroin solution with a concentration of 30 wt %, a polyethylene glycol solution with a concentration of 90 wt %, and a glycerin solution with a concentration of 70 wt % are mixed in the mass ratio of 10:5:5 to obtain an intermediate mixed solution, and then a rapamycin solution with a concentration of 1 mg/mL and/or a curcumin solution with a concentration of 1 mg/ml are added to the intermediate mixed solution to obtain the mixed solution of silk fibroin carrying drugs, the volume ratio of the intermediate mixed solution to the rapamycin solution is 4:1, and the volume ratio of the intermediate mixed solution to the curcumin solution is 4:1.

The prepared long-acting antibacterial anti-stenosis functional urethral stent is a tubular structure, consisting of three layers: inner, middle and outer layers; the middle layer is the fabric tube; the outer layer is the silk fibroin film carrying rapamycin and curcumin; the inner layer is the antibacterial antifouling coating, consisting of chitosan-nanosilica arrays, villi, microvilli and antibacterial peptide; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyethylene glycol, which is bonded with the chitosan in the chitosan-nanosilica array through covalent bonds; one end of the microvillus is fixed to the villus while the other end is a free end, and the material of the microvillus is poly(2-methacryloyloxyethyl phosphorylcholine), which is bonded with the villus through covalent bonds; the antibacterial peptide is distributed in the whole inner layer; the wall thickness of the long-acting antibacterial anti-stenosis functional urethral stent is 0.19 mm, and the wall thickness of the middle layer is 0.1 mm; the antibacterial antifouling ability of the long-acting antibacterial anti-stenosis functional urethral stent can last until the 4th day, the width of the antibacterial zone is 0.55 mm, the slow-release time of anti-stenosis drugs on the outer layer can reach 400 hours, and the cumulative release rate of the drug is 90.39%.

Example 7

A method of preparing the long-acting antibacterial anti-stenosis functional urethral stent, comprises the following steps:
(1) Preparation of Fabric Tube;
   making yarns into the fabric tube by textile molding, wherein the yarn is composed of multiple poly(lactic-co-glycolic acid) filaments with a fineness of 100 tex and a medical silver wire with developing function with a fineness of 100 tex; wherein the textile molding uses the braiding technique, the machine is an automatic 32-spindle braiding machine, the braiding structure is Hercules braid (3/3 interweave), the braiding speed is 60 rpm, the gear ratio is 82/21, and the braiding height is 35 cm;
   the prepared fabric tube is a fabric with tubular structure, and the fabric tube has a radial compression modulus of 0.54 MPa, an elastic recovery ratio of 93.63%, a circumferential expansion breaking strength of 0.73 MPa, and a yarn coverage rate of 82.31%;
(2) Pretreatment;
   first, washing the fabric tube prepared in step (1) with an oxalic acid solution with a concentration of 15 wt % at 70° C. for 60 min, then washing the fabric tube with distilled water 5 times with ultrasound before heat-setting, the temperature of heat-setting is 90° C., and the time of heat-setting is 60 min;
(3) Preparation of Antibacterial Antifouling Coating;
   (a) after coating the inner surface of the fabric tube with a nanosilica amino silicone oil modified epoxy resin mixed solution containing chitosan for 5 times (the coating thickness of each time is 0.01 mm), drying at normal temperature for 3 h, then baking and solidifying at 100° C. for 36 h to form the chitosan-nanosilica array;
   the nanosilica amino silicone oil modified epoxy resin mixed solution containing chitosan is prepared by mixing the mixed solution containing nanosilica, the chitosan solution and the silane coupling agent YDH-660 in a volume ratio of 2:1:1, then performing ultrasonic dispersion for 3 h;
   the mixed solution containing nanosilica is composed of 2.0 wt % nanosilica, 15 wt % amino silicon oil and an appropriate amount of epoxy resin;
   the concentration of the chitosan solution is 10 wt %, which is prepared by adding chitosan to an acetic acid solution with a concentration of 1.5 wt %;
   (b) after impregnating the product of step (a) in anhydrous toluene solution containing initiator (the concentration of the initiator is 7 mM, and the initiator is trichlorosilane) to react at normal temperature for 10 h, rinsing with anhydrous toluene, then drying at 100° C. in a vacuum environment (vacuum degree is 0.09 MPa) for 3 h;
   (c) sealing the product of step (b) in a tubular reactor, degassing and placing at a temperature of 20° C. and under the protection of neon, then injecting a polymeric solution into the tubular reactor until the product of step (b) is completely submerged and keeping for 24 h;
   the polymeric solution is a solution containing ethylene oxide; the content of ethylene oxide in the polymeric solution is 15 wt %;
   the preparation process of the solution containing ethylene oxide is: dissolving ethylene oxide in methanol at 20° C., after adding the catalyst, stirring and degassing under the protection of neon for 20 min; the catalyst is a mixture of copper bromide, cuprous bromide and 2,2-bipyridine with a mass ratio of 1:2:8, and the mass ratio of the catalyst to ethylene oxide is 2:25;
   (d) after impregnating the product of step (c) in anhydrous toluene solution containing initiator (the concentration of the initiator is 7 mM, and the initiator is trichlorosilane) to react at normal temperature for 10 h, rinsing with anhydrous toluene, then drying at 100° C. in a vacuum environment (vacuum degree is 0.09 MPa) for 3 h;
   (e) sealing the product of step (d) in a tubular reactor, degassing and placing at a temperature of 20° C. and under the protection of neon, then injecting a polymeric solution into the tubular reactor until the product of step (d) is completely submerged and keeping for 24 h;
   the polymeric solution is a solution containing carboxybetaine methacrylate; the content of carboxybetaine methacrylate in the polymeric solution is 15 wt %;
   the preparation process of the solution containing carboxybetaine methacrylate is: dissolving carboxybetaine methacrylate in methanol at 20° C., after adding the catalyst, stirring and degassing under the protection of neon for 20 min; the catalyst is a mixture of copper bromide, cuprous bromide and 2,2-bipyridine with a mass ratio of 1:2:8, and the mass ratio of the catalyst to carboxybetaine methacrylate is 2:25;
   (f) washing the product of step (e) with deionized water and methanol before drying, then impregnating in a clarithromycin solution with a concentration of 3 mg/mL at 25° C. for 40 min to form the antibacterial antifouling coating on the inner surface of the fabric tube;
(4) Preparation of the Silk Fibroin Film Carrying Rapamycin;
   using the coating brush to evenly coat the outer surface of the fabric tube with the mixed solution of silk fibroin carrying drugs for 5 times, with the coating thickness of 0.01 mm each time, forming the film by air-drying at 4° C., then carrying out the ultraviolet irradiation (power 15 W for 2 h), pre-cooling (at −80° C. for 20 h) and freeze-drying (at −80° C. for 48 h) successively to obtain the long-acting antibacterial anti-stenosis functional urethral stent;

the preparation process of the mixed solution of silk fibroin carrying drugs is: first, a silk fibroin solution with a concentration of 30 wt %, a polyethylene glycol solution with a concentration of 90 wt %, and a glycerin solution with a concentration of 70 wt % are mixed in the mass ratio of 10:5:5 to obtain an intermediate mixed solution, and then a rapamycin solution with a concentration of 1.5 mg/mL is added to the intermediate mixed solution to obtain the mixed solution of silk fibroin carrying drugs, and the volume ratio of the intermediate mixed solution to the rapamycin solution is 4:1.

The prepared long-acting antibacterial anti-stenosis functional urethral stent is a tubular structure, consisting of three layers: inner, middle and outer layers; the middle layer is the fabric tube; the outer layer is the silk fibroin film carrying rapamycin; the inner layer is the antibacterial antifouling coating, consisting of chitosan-nanosilica arrays, villi, microvilli and clarithromycin; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is polyether, which is bonded with the chitosan in the chitosan-nanosilica array through covalent bonds; one end of the microvillus is fixed to the villus while the other end is a free end, and the material of the microvillus is carboxybetaine polymethacrylate, which is bonded with the villus through covalent bonds; the clarithromycin is distributed in the whole inner layer; the wall thickness of the long-acting antibacterial anti-stenosis functional urethral stent is 0.23 mm, and the wall thickness of the middle layer is 0.13 mm; the antibacterial antifouling ability of the long-acting antibacterial anti-stenosis functional urethral stent can last until the 4th day, the width of the antibacterial zone is 0.61 mm, the slow-release time of anti-stenosis drugs on the outer layer can reach 400 hours, and the cumulative release rate of the drug is 85.93%.

Example 8

A method of preparing the long-acting antibacterial anti-stenosis functional urethral stent, comprises the following steps:

(1) Preparation of Fabric Tube;

making yarns into the fabric tube by textile molding, wherein the yarn is composed of multiple polylactide filaments with a fineness of 100 tex and polydiaxone filaments with a fineness of 100 tex with a mass ratio of 1:1; wherein the textile molding uses the braiding technique, the machine is an automatic 48-spindle braiding machine, the braiding structure is three-direction braided structure (three-direction braided structure: adding axial yarns on the basis of regular braided structure), the braiding speed is 70 rpm, the gear ratio is 82/44, and the braiding height is 40 cm;

the prepared fabric tube is a fabric with tubular structure, and the fabric tube has a radial compression modulus of 1.39 MPa, an elastic recovery ratio of 92.67%, a circumferential expansion breaking strength of 0.83 MPa, and a yarn coverage rate of 82.16%;

(2) Pretreatment;

first, washing the fabric tube prepared in step (1) with an oxalic acid solution with a concentration of 15 wt % at 70° C. for 60 min, then washing the fabric tube with distilled water 5 times with ultrasound before heat-setting, the temperature of heat-setting is 80° C., and the time of heat-setting is 60 min;

(3) Preparation of Antibacterial Antifouling Coating;

(a) after coating the inner surface of the fabric tube with a nanosilica amino silicone oil modified epoxy resin mixed solution containing chitosan for 5 times (the coating thickness of each time is 0.01 mm), drying at normal temperature for 3 h, then baking and solidifying at 100° C. for 36 h to form the chitosan-nanosilica array;

the nanosilica amino silicone oil modified epoxy resin mixed solution containing chitosan is prepared by mixing the mixed solution containing nanosilica, the chitosan solution and the silane coupling agent YDH-660 in a volume ratio of 2:1:1, then performing ultrasonic dispersion for 3 h;

the mixed solution containing nanosilica is composed of 2.0 wt % nanosilica, 15 wt % amino silicon oil and an appropriate amount of epoxy resin;

the concentration of the chitosan solution is 10 wt %, which is prepared by adding chitosan to an acetic acid solution with a concentration of 1.5 wt %;

(b) after impregnating the product of step (a) in anhydrous toluene solution containing initiator (the concentration of the initiator is 7 mM, and the initiator is trichlorosilane) to react at normal temperature for 10 h, rinsing with anhydrous toluene, then drying at 100° C. in a vacuum environment (vacuum degree is 0.09 MPa) for 3 h;

(c) sealing the product of step (b) in a tubular reactor, degassing and placing at a temperature of 20° C. and under the protection of neon, then injecting a polymeric solution into the tubular reactor until the product of step (b) is completely submerged and keeping for 17 h;

the polymeric solution is a solution containing vinyl acetate and a solution containing ethylene glycol with a mass ratio of 1:1; the content of vinyl acetate in the solution containing vinyl acetate is 15 wt %; the content of ethylene glycol in the solution containing ethylene glycol is 15 wt %;

the preparation process of the solution containing vinyl acetate is: dissolving vinyl acetate in methanol at 20° C., after adding the catalyst, stirring and degassing under the protection of neon for 20 min;

the preparation process of the solution containing ethylene glycol is: dissolving ethylene glycol in methanol at 20° C., after adding the catalyst, stirring and degassing under the protection of neon for 20 min;

the catalyst is a mixture of copper bromide, cuprous bromide and 2,2-bipyridine with a mass ratio of 1:2:8; the mass ratio of the catalyst to vinyl acetate is 2:25; the mass ratio of the catalyst to ethylene glycol is 2:25;

(d) after impregnating the product of step (c) in anhydrous toluene solution containing initiator (the concentration of the initiator is 7 mM, and the initiator is trichlorosilane) to react at normal temperature for 10 h, rinsing with anhydrous toluene, then drying at 100° C. in a vacuum environment (vacuum degree is 0.09 MPa) for 3 h;

(e) sealing the product of step (d) in a tubular reactor, degassing and placing at a temperature of 20° C. and under the protection of neon, then injecting a polymeric solution into the tubular reactor until the product of step (d) is completely submerged and keeping for 17 h;

the polymeric solution is a solution containing 2-methyl-2-oxazoline and a solution containing 2-methacryloyloxyethyl phosphorylcholine with a mass ratio of 1:1; the content of 2-methyl-2-oxazoline in the solution containing 2-methyl-2-oxazoline is 15 wt %; the content of 2-methacryloyloxyethyl phosphorylcholine in the solution containing 2-methacryloyloxyethyl phosphorylcholine is 15 wt %;

the preparation process of the solution containing 2-methyl-2-oxazoline is: dissolving 2-methyl-2-oxazoline in methanol at 20° C., after adding the catalyst, stirring and degassing under the protection of neon for 20 min;

the preparation process of the solution containing 2-methacryloyloxyethyl phosphorylcholine is: dissolving 2-methacryloyloxyethyl phosphorylcholine in methanol at 20° C., after adding the catalyst, stirring and degassing under the protection of neon for 20 min;

the catalyst is a mixture of copper bromide, cuprous bromide and 2,2-bipyridine with a mass ratio of 1:2:8; the mass ratio of the catalyst to 2-methyl-2-oxazoline is 2:25; the mass ratio of the catalyst to 2-methacryloyloxyethyl phosphorylcholine is 2:25;

(f) washing the product of step (e) with deionized water and methanol before drying, then impregnating in a sparfloxacin solution with a concentration of 4 mg/mL at 25° C. for 40 min to form the antibacterial antifouling coating on the inner surface of the fabric tube;

(4) Preparation of the Silk Fibroin Film Carrying Curcumin;

using the coating brush to evenly coat the outer surface of the fabric tube with the mixed solution of silk fibroin carrying drugs for 5 times, with the coating thickness of 0.01 mm each time, forming the film by air-drying at 4° C., then carrying out the steam treatment (at 70° C. for 5 h), pre-cooling (at −80° C. for 24 h) and freeze-drying (at −75° C. for 60 h) successively to obtain the long-acting antibacterial anti-stenosis functional urethral stent;

the preparation process of the mixed solution of silk fibroin carrying drugs is: first, a silk fibroin solution with a concentration of 15 wt %, a polyethylene glycol solution with a concentration of 45 wt %, and a glycerin solution with a concentration of 35 wt % are mixed in the mass ratio of 10:5:3 to obtain an intermediate mixed solution, and then a curcumin solution with a concentration of 3.0 mg/mL is added to the intermediate mixed solution to obtain the mixed solution of silk fibroin carrying drugs, and the volume ratio of the intermediate mixed solution to the curcumin solution is 4:1.

The prepared long-acting antibacterial anti-stenosis functional urethral stent is a tubular structure, consisting of three layers: inner, middle and outer layers; the middle layer is the fabric tube; the outer layer is the silk fibroin film carrying curcumin; the inner layer is the antibacterial antifouling coating, consisting of chitosan-nanosilica arrays, villi, microvilli and sparfloxacin; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is a mixture of polyvinyl alcohol and polyethylene glycol, which is bonded with the chitosan in the chitosan-nanosilica array through covalent bonds; one end of the microvillus is fixed to the villus while the other end is a free end, and the material of the microvillus is a mixture of poly(2-methyl-2-oxazoline) and poly(2-methacryloyloxyethyl phosphorylcholine), which is bonded with the villus through covalent bonds; the sparfloxacin is distributed in the whole inner layer; the wall thickness of the long-acting antibacterial anti-stenosis functional urethral stent is 0.25 mm, and the wall thickness of the middle layer is 0.15 mm; the antibacterial antifouling ability of the long-acting antibacterial anti-stenosis functional urethral stent can last until the 4th day, the width of the antibacterial zone is 0.67 mm, the slow-release time of anti-stenosis drugs on the outer layer can reach 400 hours, and the cumulative release rate of the drug is 76.44%.

Figure 4:
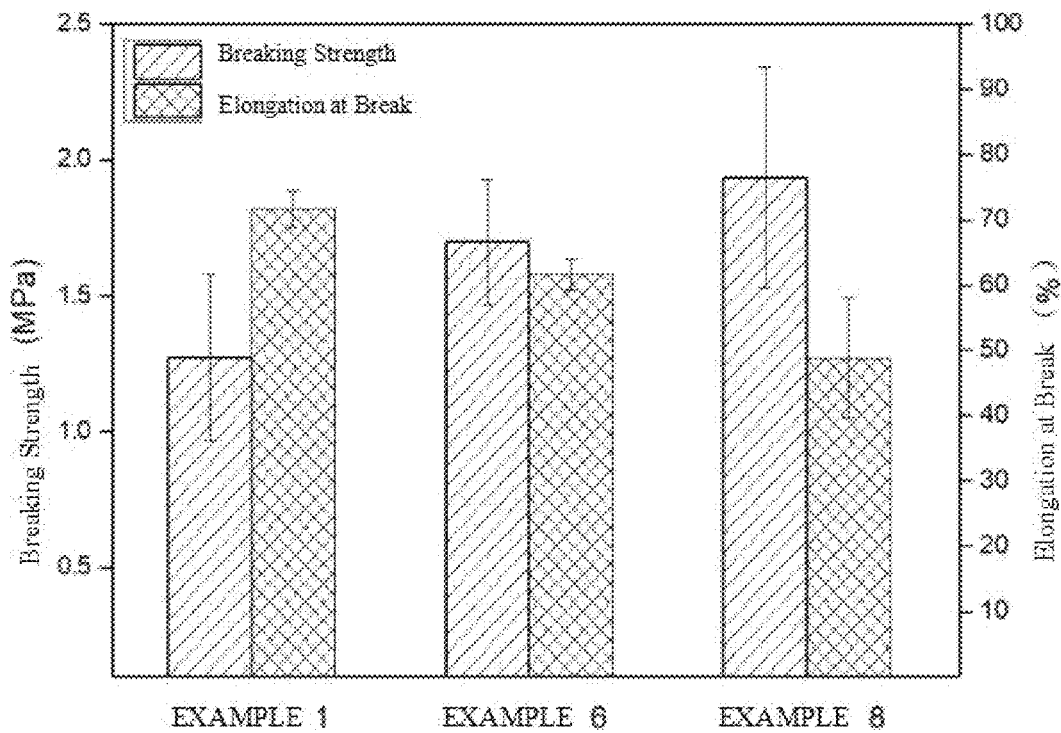
FIG. 4 is a diagram of the circumferential expansion mechanical properties of the long-acting antibacterial anti-stenosis functional urethral stent prepared in Examples 1, 6 and 8.

FIG. 4 is a diagram of the circumferential expansion mechanical properties of the long-acting antibacterial anti-stenosis functional urethral stent prepared in Examples 1, 6 and 8, which can be concluded from the results that the circumferential expansion breaking strength ranges from 1.25-1.89 MPa, and the elongation at break ranges from 48.56-73.85%.

Figure 5:
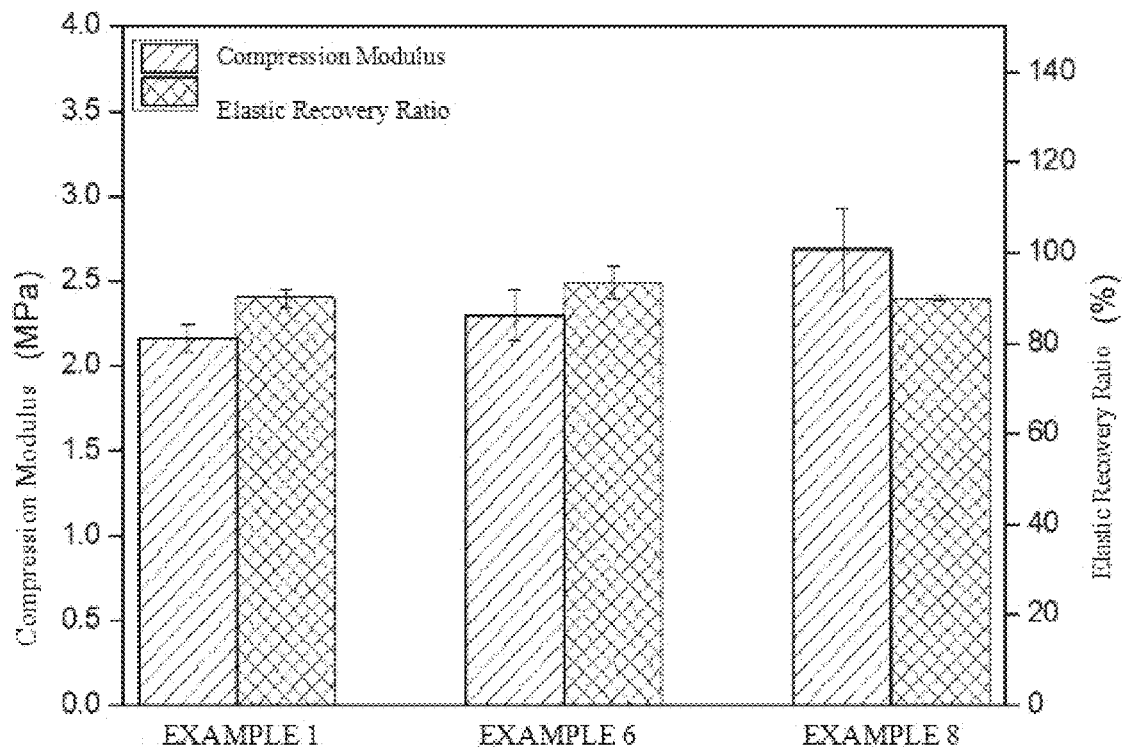
FIG. 5 is a 100-cycle anti-stenosis property test chart of the long-acting antibacterial anti-stenosis functional urethral stent prepared in Examples 1, 6, and 8.

FIG. 5 is a 100-cycle anti-stenosis property test chart of the long-acting antibacterial anti-stenosis functional urethral stent prepared in Examples 1, 6, and 8, which can be concluded from the results that the radial compression modulus of the urethral stent ranges from 2.16-2.68 MPa, and the elastic recovery ratio ranges from 89.87-93.46%.

Example 9

A method of preparing the long-acting antibacterial anti-stenosis functional urethral stent, comprises the following steps:

(1) Preparation of Fabric Tube;

making yarns into the fabric tube by textile molding, wherein the yarn is composed of multiple silk filaments with a fineness of 100 tex and polyglycolide acid filaments with a fineness of 100 tex with a mass ratio of 1:1; wherein the textile molding uses the braiding technique, the machine is an automatic 64-spindle braiding machine, the braiding structure uses diamond braid (1/1 interweave) and regular braid (2/2 interweave) with a mass ratio of 1:1, the braiding speed is 100 rpm, the gear ratio is 82/21, and the braiding height is 50 cm;

the prepared fabric tube is a fabric with tubular structure, and the fabric tube has a radial compression modulus of 0.67 MPa, an elastic recovery ratio of 87.16%, a circumferential expansion breaking strength of 0.59 MPa, and a yarn coverage rate of 80.53%;

(2) Pretreatment;

first, washing the fabric tube prepared in step (1) with an oxalic acid solution with a concentration of 1 wt % at 50° C. for 30 min, then washing the fabric tube with distilled water 2 times with ultrasound before heat-setting, the temperature of heat-setting is 95° C., and the time of heat-setting is 40 min;

(3) Preparation of Antibacterial Antifouling Coating;

(a) after coating the inner surface of the fabric tube with a nanosilica amino silicone oil modified epoxy resin mixed solution containing chitosan for 1 time (the coating thickness is 0.02 mm), drying at normal temperature for 0.5 h, then baking and solidifying at 80° C. for 24 h to form the chitosan-nanosilica array;

the nanosilica amino silicone oil modified epoxy resin mixed solution containing chitosan is prepared by mixing the mixed solution containing nanosilica, the chitosan solution and the silane coupling agent YDH-660 in a volume ratio of 2:2:1, then performing ultrasonic dispersion for 3 h;

the mixed solution containing nanosilica is composed of 0.1 wt % nanosilica, 5 wt % amino silicon oil and an appropriate amount of epoxy resin;

the concentration of the chitosan solution is 1 wt %, which is prepared by adding chitosan to an acetic acid solution with a concentration of 0.5 wt %;

(b) after impregnating the product of step (a) in anhydrous toluene solution containing initiator (the concentration of the initiator is 5 mM, and the initiator is ω-mercaptoundecyl bromoisobutyrate) to react at normal temperature for 10 h, rinsing with anhydrous toluene, then drying at 50° C. in a vacuum environment (vacuum degree is 0.09 MPa) for 3 h;

(c) sealing the product of step (b) in a tubular reactor, degassing and placing at a temperature of 20° C. and under the protection of nitrogen, then injecting a polymeric solution into the tubular reactor until the product of step (b) is completely submerged and keeping for 20 h;

the polymeric solution is a solution containing the mixture of acrylic acid and hydroxypropyl acrylate; the content of the mixture of acrylic acid and hydroxypropyl acrylate in the polymeric solution is 10 wt %;

the preparation process of the solution containing the mixture of acrylic acid and hydroxypropyl acrylate is: dissolving the mixture of acrylic acid and hydroxypropyl acrylate (mass ratio as 1:1) in methanol at 20° C., after adding the catalyst, stirring and degassing under the protection of nitrogen for 15 min; the catalyst is a mixture of copper bromide, cuprous bromide and 2,2-bipyridine with a mass ratio of 1:6:24, and the mass ratio of the catalyst to the mixture of acrylic acid and hydroxypropyl acrylate is 2:25;

(d) after impregnating the product of step (c) in anhydrous toluene solution containing initiator (the concentration of the initiator is 5 mM, and the initiator is ω-mercaptoundecyl bromoisobutyrate) to react at normal temperature for 10 h, rinsing with anhydrous toluene, then drying at 50° C. in a vacuum environment (vacuum degree is 0.09 MPa) for 3 h;

(e) sealing the product of step (d) in a tubular reactor, degassing and placing at a temperature of 20° C. and under the protection of nitrogen, then injecting a polymeric solution into the tubular reactor until the product of step (d) is completely submerged and keeping for 20 h;

the polymeric solution is a solution containing sulfobetaine methacrylic acid, and the content of the sulfobetaine methacrylic acid in the polymeric solution is 10 wt %;

the preparation process of the solution containing sulfobetaine methacrylic acid is: dissolving sulfobetaine methacrylic acid in methanol at 20° C., after adding the catalyst, stirring and degassing under the protection of nitrogen for 15 min; the catalyst is a mixture of copper bromide, cuprous bromide and 2,2-bipyridine with a mass ratio of 1:6:24, and the mass ratio of the catalyst to sulfobetaine methacrylic acid is 2:25;

(f) washing the product of step (e) with deionized water and methanol before drying, then impregnating in a amikacin solution with a concentration of 0.1 mg/mL at 25° C. for 20 min to form the antibacterial antifouling coating on the inner surface of the fabric tube;

(4) Preparation of the Silk Fibroin Film Carrying Rapamycin and Curcumin;

using the coating brush to evenly coat the outer surface of the fabric tube with the mixed solution of silk fibroin carrying drugs for 1 time, with the coating thickness of 0.02 mm, forming the film by air-drying at 4° C., then carrying out pre-cooling (at −80° C. for 3 h) and freeze-drying (at −70° C. for 72 h) successively to obtain the long-acting antibacterial anti-stenosis functional urethral stent;

the preparation process of the mixed solution of silk fibroin carrying drugs is: first, a silk fibroin solution with a concentration of 20 wt %, a polyethylene glycol solution with a concentration of 10 wt %, and a glycerin solution with a concentration of 5 wt % are mixed in the mass ratio of 10:5:3 to obtain an intermediate mixed solution, and then a rapamycin solution with a concentration of 0.5 mg/mL and a curcumin solution with a concentration of 0.5 mg/ml are added to the intermediate mixed solution to obtain the mixed solution of silk fibroin carrying drugs, the volume ratio of the intermediate mixed solution to the rapamycin solution is 4:1, and the volume ratio of the intermediate mixed solution to the curcumin solution is 4:1.

The prepared long-acting antibacterial anti-stenosis functional urethral stent is a tubular structure, consisting of three layers: inner, middle and outer layers; the middle layer is the fabric tube; the outer layer is the silk fibroin film carrying rapamycin and curcumin; the inner layer is the antibacterial antifouling coating, consisting of chitosan-nanosilica arrays, villi, microvilli and amikacin; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is acrylic acid-hydroxypropyl acrylate copolymer, which is bonded with the chitosan in the chitosan-nanosilica array through covalent bonds; one end of the microvillus is fixed to the villus while the other end is a free end, and the material of the microvillus is polymethacrylate sulfobetaine, which is bonded with the villus through covalent bonds; the amikacin is distributed in the whole inner layer; the wall thickness of the long-acting antibacterial anti-stenosis functional urethral stent is 0.22 mm, and the wall thickness of the middle layer is 0.18 mm; the antibacterial antifouling ability of the long-acting antibacterial anti-stenosis functional urethral stent can last until the 3rd day, the width of the antibacterial zone is 0.28 mm, the slow-release time of anti-stenosis drugs on the outer layer can reach 400 hours, and the cumulative release rate of the drug is 82.96%.

Example 10

A method of preparing the long-acting antibacterial anti-stenosis functional urethral stent, basically is the same as in Example 9, except that in step (f), impregnating in a mixed solution of amikacin and ketolovic acid with a concentration of 5 mg/mL, and the mass ratio of amikacin and ketolovic acid is 1:1.

The prepared long-acting antibacterial anti-stenosis functional urethral stent is a tubular structure, consisting of three layers: inner, middle and outer layers; the middle layer is the fabric tube; the outer layer is the silk fibroin film carrying rapamycin and curcumin; the inner layer is the antibacterial antifouling coating, consisting of chitosan-nanosilica arrays, villi, microvilli, amikacin, and ketolovic acid; the chitosan-nanosilica array arranged on the inner surface of the fabric tube, is a nanosilica array carrying chitosan molecules; one end of the villus is fixed on the surface of the chitosan-nanosilica array while the other end is a free end, and the material of the villus is acrylic acid-hydroxypropyl acrylate copolymer, which is bonded with the chitosan in the chitosan-nanosilica array through covalent bonds; one end of the microvillus is fixed to the villus while the other end is a free end, and the material of the microvillus is polymethacrylate sulfobetaine, which is bonded with the villus through covalent bonds; the amikacin and ketolovic acid is distributed in the whole inner layer; the wall thickness of the long-acting antibacterial anti-stenosis functional urethral stent is 0.22 mm, and the wall thickness of the middle layer is 0.18 mm; the antibacterial antifouling ability of the long-acting antibacterial anti-stenosis functional urethral stent can last until the 5th day, the width of the antibacterial zone is 0.47 mm, the slow-release time of anti-stenosis drugs on the outer layer can reach 400 hours, and the cumulative release rate of the drug is 82.17%.

Example 11

A method of preparing the long-acting antibacterial anti-stenosis functional urethral stent, basically is the same as in Example 1, except that the textile molding of the fabric tube uses the knitting technique, and the knitting structure is rib stitch.

The prepared fabric tube is a fabric with tubular structure, with the transverse coil density as 30 rows/5 cm, the longitudinal coil density as 30 columns/5 cm, the coil length as 5 mm, and total density as 3000 coils/25 cm$^2$; the fabric tube has a radial compression modulus of 2.15 MPa, an elastic recovery ratio of 75.57%, a circumferential expansion breaking strength of 4.83 MPa, and a yarn coverage rate of 82.34%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.29 mm, and the wall thickness of the middle layer is 0.26 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 88.45%.

Example 12

A method of preparing the long-acting antibacterial anti-stenosis functional urethral stent, basically is the same as in Example 1, except that the textile molding of the fabric tube uses the knitting technique, and the knitting structure is double-sided plain stitch.

The prepared fabric tube is a fabric with tubular structure, with the transverse coil density as 35 rows/5 cm, the longitudinal coil density as 35 columns/5 cm, the coil length as 4 mm, and total density as 3500 coils/25 cm$^2$; the fabric tube has a radial compression modulus of 3.11 MPa, an elastic recovery ratio of 77.62%, a circumferential expansion breaking strength of 5.69 MPa, and a yarn coverage rate of 82.48%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.26 mm, and the wall thickness of the middle layer is 0.23 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 87.76%.

Example 13

A method of preparing the long-acting antibacterial anti-stenosis functional urethral stent, basically is the same as in Example 1, except that the textile molding of the fabric tube uses the knitting technique, and the knitting structure is warp plain stitch.

The prepared fabric tube is a fabric with tubular structure, with the transverse coil density as 40 rows/5 cm, the longitudinal coil density as 40 columns/5 cm, the coil length as 6 mm, and total density as 4000 coils/25 cm$^2$; the fabric tube has a radial compression modulus of 4.73 MPa, an elastic recovery ratio of 76.93%, a circumferential expansion breaking strength of 6.12 MPa, and a yarn coverage rate of 79.74%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.24 mm, and the wall thickness of the middle layer is 0.21 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 87.43%.

Example 14

A method of preparing the long-acting antibacterial anti-stenosis functional urethral stent, basically is the same as in Example 1, except that the textile molding of the fabric tube uses the knitting technique, and the knitting structure is eyelet stitch.

The prepared fabric tube is a fabric with tubular structure, with the transverse coil density as 60 rows/5 cm, the longitudinal coil density as 55 columns/5 cm, the coil length as 6 mm, and total density as 2000 coils/25 cm$^2$; the fabric tube has a radial compression modulus of 3.65 MPa, an elastic recovery ratio of 75.18%, a circumferential expansion breaking strength of 3.78 MPa, and a yarn coverage rate of 66.67%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.3 mm, and the wall thickness of the middle layer is 0.27 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 88.16%.

Example 15

A method of preparing the long-acting antibacterial anti-stenosis functional urethral stent, basically is the same as in Example 1, except that the textile molding of the fabric tube uses the knitting technique, and the knitting structure uses warp plain stitch and rib stitch with a mass ratio of 1:1.

The prepared fabric tube is a fabric with tubular structure, with the transverse coil density as 70 rows/5 cm, the longitudinal coil density as 65 columns/5 cm, the coil length as 3 mm, and total density as 2500 coils/25 $cm^2$; the fabric tube has a radial compression modulus of 2.34 MPa, an elastic recovery ratio of 76.45%, a circumferential expansion breaking strength of 6.26 MPa, and a yarn coverage rate of 75.14%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.28 mm, and the wall thickness of the middle layer is 0.25 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 87.55%.

Example 16

A method of preparing the long-acting antibacterial anti-stenosis functional urethral stent, basically is the same as in Example 1, except that the textile molding of the fabric tube uses the machine weaving technique, and the machine weaving structure is twill weave.

The prepared fabric tube is a fabric with tubular structure, with the warp density as 200 pieces/10 cm, and the weft density as 200 pieces/10 cm; the fabric tube has a radial compression modulus of 2.74 MPa, an elastic recovery ratio of 89.67%, a circumferential expansion breaking strength of 7.50 MPa, and a yarn coverage rate of 78.93%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.20 mm, and the wall thickness of the middle layer is 0.17 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 88.27%.

Example 17

A method of preparing the long-acting antibacterial anti-stenosis functional urethral stent, basically is the same as in Example 1, except that the textile molding of the fabric tube uses the machine weaving technique, and the machine weaving structure is satin weave.

The prepared fabric tube is a fabric with tubular structure, with the warp density as 400 pieces/10 cm, and the weft density as 400 pieces/10 cm; the fabric tube has a radial compression modulus of 3.46 MPa, an elastic recovery ratio of 91.37%, a circumferential expansion breaking strength of 8.49 MPa, and a yarn coverage rate of 80.21%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.19 mm, and the wall thickness of the middle layer is 0.16 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 88.35%.

Example 18

A method of preparing the long-acting antibacterial anti-stenosis functional urethral stent, basically is the same as in Example 1, except that the textile molding of the fabric tube uses the machine weaving technique, and the machine weaving structure is warp rib weave.

The prepared fabric tube is a fabric with tubular structure, with the warp density as 800 pieces/10 cm, and the weft density as 800 pieces/10 cm; the fabric tube has a radial compression modulus of 3.97 MPa, an elastic recovery ratio of 92.10%, a circumferential expansion breaking strength of 8.61 MPa, and a yarn coverage rate of 79.93%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.20 mm, and the wall thickness of the middle layer is 0.17 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 89.61%.

Example 19

A method of preparing the long-acting antibacterial anti-stenosis functional urethral stent, basically is the same as in Example 1, except that the textile molding of the fabric tube uses the machine weaving technique, and the machine weaving structure is honeycomb weave.

The prepared fabric tube is a fabric with tubular structure, with the warp density as 1600 pieces/10 cm, and the weft density as 1600 pieces/10 cm; the fabric tube has a radial compression modulus of 4.76 MPa, an elastic recovery ratio of 91.51%, a circumferential expansion breaking strength of 9.72 MPa, and a yarn coverage rate of 82.53%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.21 mm, and the wall thickness of the middle layer is 0.18 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 87.42%.

Example 20

A method of preparing the long-acting antibacterial anti-stenosis functional urethral stent, basically is the same as in Example 1, except that the textile molding of the fabric tube uses the machine weaving technique, and the machine weaving structure uses plain weave and twill weave with a mass ratio of 1:1.

The prepared fabric tube is a fabric with tubular structure, with the warp density as 2000 pieces/10 cm, and the weft density as 2000 pieces/10 cm; the fabric tube has a radial compression modulus of 5.72 MPa, an elastic recovery ratio of 93.25%, a circumferential expansion breaking strength of 10.62 MPa, and a yarn coverage rate of 83.15%.

The prepared long-acting antibacterial anti-stenosis functional urethral stent is a tubular structure, consisting of three layers: inner, middle and outer layers; the middle layer is the fabric tube, that is a fabric with tubular structure; the outer layer is the silk fibroin film carrying anti-stenosis drugs; the inner layer is the antibacterial antifouling coating; the wall thickness of the long-acting antibacterial anti-stenosis functional urethral stent is 0.22 mm, and the wall thickness of the middle layer is 0.19 mm; the antibacterial antifouling ability of the long-acting antibacterial anti-stenosis functional urethral stent can last until the 4th day, the width of the antibacterial zone is 0.38 mm, the slow-release time of anti-stenosis drugs on the outer layer can reach 400 hours, and the cumulative release rate of the drug is 88.36%.

Example 21

A method of preparing the long-acting antibacterial anti-stenosis functional urethral stent, basically is the same as in Example 3, except that the concentration of the curcumin solution is 1.6 mg/mL.

Example 22

A method of preparing the long-acting antibacterial anti-stenosis functional urethral stent, basically is the same as in Example 3, except that the concentration of the curcumin solution is 4.0 mg/mL.

Figure 7:
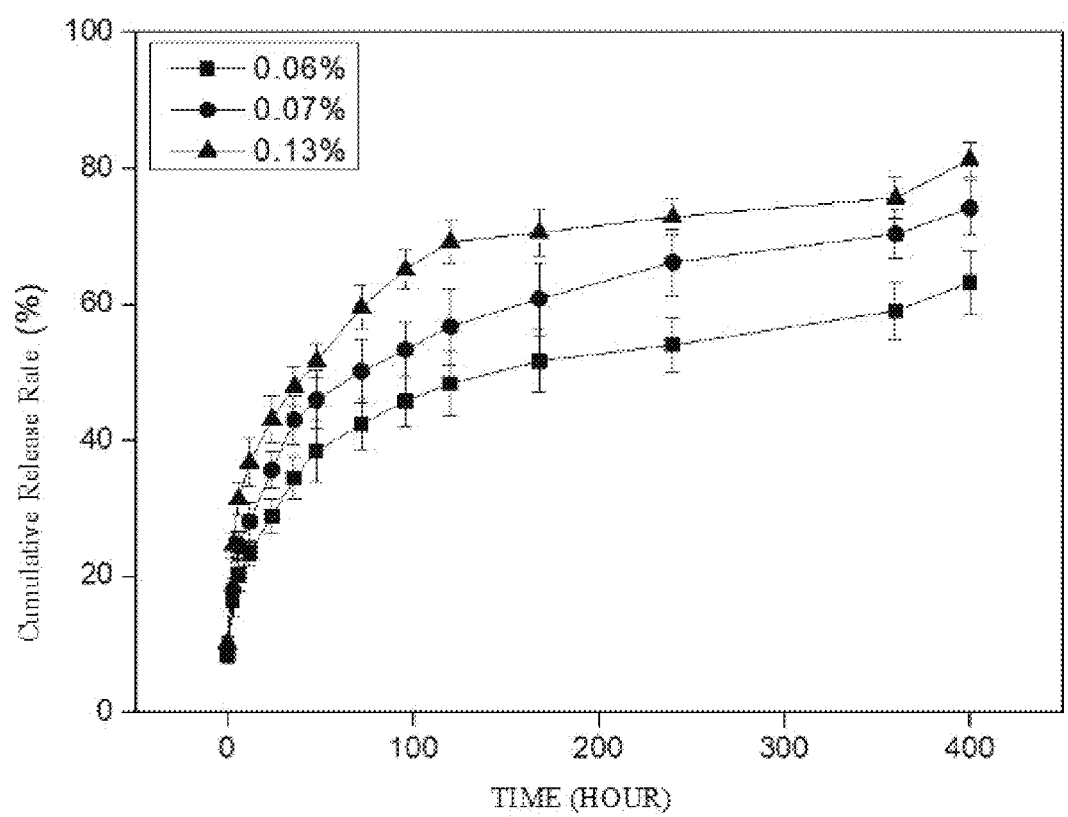
FIG. 7 is the drug release curve of the silk fibroin film carrying anti-stenosis drugs (curcumin) in the long-acting antibacterial anti-stenosis functional urethral stent prepared in Examples 3, 21, and 22.

FIG. 7 is the drug release curve of the silk fibroin film carrying curcumin in the long-acting antibacterial anti-stenosis functional urethral stent prepared in Examples 3, 21, and 22; three groups of drug films with different mass fractions continuously release drugs within 400 h and reach the maximum release rate at the 400th hour; wherein the curcumin film with a mass fraction of 0.13% (prepared in Example 22) has the highest cumulative release rate of (81.35±3.21)%. It can be seen that the cumulative release rate of curcumin increases with the mass fraction of the curcumin film, and the cumulative release rate has also been significantly improved; compared with the drug film with the mass fraction of 0.13%, the other two groups of drug films show a certain decrease in cumulative drug release rate, the curcumin film with a mass fraction of 0.07% (prepared in Example 21) has the cumulative release rate of (74.23±3.57)%, while the curcumin film with a mass fraction of 0.06% (prepared in Example 3) has the cumulative release rate of (63.25±4.65)%, indicating that the curcumin drug film with a mass fraction of 0.13% has the best drug release property and can ensure sufficient utilization of the drug.

The invention claimed is:
1. A long-acting antibacterial anti-stenosis functional urethral stent, wherein the urethral stent is a tubular structure consisting of three layers: inner, middle and outer layers;
wherein the middle layer is a fabric tube; wherein the outer layer is a silk fibroin film carrying anti-stenosis drugs; wherein the inner layer is an antibacterial antifouling coating, consisting of chitosan-nanosilica arrays, villi, microvilli and antibacterial drugs;
wherein the chitosan-nanosilica array arranged on an inner surface of the fabric tube, is a nanosilica array carrying chitosan molecules; one end of the villus is fixed on a surface of the chitosan-nanosilica array while the other end is a free end, and a material of the villus is a polymer containing polyhydroxy functional group, which is bonded with the chitosan in the chitosan-nanosilica array through covalent bonds, and a number of hydroxyl of the polymer containing polyhydroxy functional group is greater than or equal to 2; one end of the microvillus is fixed to the villus while the other end is a free end, and a material of the microvillus is a polymer with antibacterial adhesion function, which is bonded with the villus through covalent bonds; wherein the antibacterial drug is distributed in the whole inner layer,
wherein the fabric tube consists of yarns; wherein the yarn is one or more selected from the group consisting of silk, a polylactide filament, a polydiaxone filament, a polyglycolide acid filament, a poly (lactic-co-glycolic acid) filament and a developing wire;
wherein the fabric tube has a radial compression modulus of 0.03-5.72 MPa, an elastic recovery ratio of 74.53-93.63%, a circumferential expansion breaking strength of 0.03-10.62 MPa, and a yarn coverage rate of 66.67-83.15%;
wherein the anti-stenosis drug is rapamycin and/or curcumin;
wherein the polymer containing polyhydroxy functional group is one or more selected from the group consisting of polyether, polyvinyl alcohol, polyethylene glycol, polyhydroxyethyl methacrylate and acrylic acid-hydroxypropyl acrylate copolymer;
wherein the polymer with antibacterial adhesion function is one or more selected from the group consisting of cationic polymer, anionic polymer, nonionic polymer and zwitterionic hydrophilic polymer;
wherein the antibacterial drug is one or more selected from the group consisting of antibacterial peptide, triclosan, heparin, clarithromycin, berberine, sparfloxacin, amikacin and ketolovic acid.
2. The long-acting antibacterial anti-stenosis functional urethral stent of claim 1, wherein a wall thickness of the long-acting antibacterial anti-stenosis functional urethral stent is 0.19-0.4 mm, and a wall thickness of the middle layer is 0.06-0.27 mm.

3. The long-acting antibacterial anti-stenosis functional urethral stent of claim 1, wherein the developing wire is a medical magnesium wire, a medical tantalum wire or a medical silver wire;
   wherein the polymer with antibacterial adhesion function is one or more selected from the group consisting of polyvinylpyridine, phosphoylcholine polymer, sulphobetaine polymer, carboxybetaine polymer, polyethylene glycol and poly(2-methyl-2-oxazoline).

* * * * *